US009687367B2

(12) United States Patent
Gill et al.

(10) Patent No.: US 9,687,367 B2
(45) Date of Patent: Jun. 27, 2017

(54) ESOPHAGEAL STENT

(71) Applicant: Merit Medical Systems, Inc., South Jordan, UT (US)

(72) Inventors: Darla Gill, Salt Lake City, UT (US); Zeke Eller, Dallas, TX (US); Rich Snider, Dallas, TX (US); Trent Clegg, Lehi, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 0 days.

(21) Appl. No.: 13/909,427

(22) Filed: Jun. 4, 2013

(65) Prior Publication Data

US 2013/0325141 A1 Dec. 5, 2013

Related U.S. Application Data

(60) Provisional application No. 61/655,807, filed on Jun. 5, 2012.

(51) Int. Cl.
*A61F 2/90* (2013.01)
*A61F 2/24* (2006.01)
(Continued)

(52) U.S. Cl.
CPC .............. *A61F 2/90* (2013.01); *A61F 2/2418* (2013.01); *A61F 2/915* (2013.01);
(Continued)

(58) Field of Classification Search
CPC ...... A61F 2/02; A61F 2/04; A61F 2/06; A61F 2002/044; A61F 2/82; A61F 2002/821;
(Continued)

(56) References Cited

U.S. PATENT DOCUMENTS 5,061,275 A * 10/1991 Wallsten et al. ............. 623/1.22
5,152,797 A   10/1992 Luckman et al.
(Continued)

FOREIGN PATENT DOCUMENTS

CN      1433818 A    8/2003
CN     201200504    3/2009
(Continued)

OTHER PUBLICATIONS

Office Action dated Jun. 19, 2014 for U.S. Appl. No. 13/153,150.
(Continued)

*Primary Examiner* — Christopher D Prone
*Assistant Examiner* — Rokhaya Diop
(74) *Attorney, Agent, or Firm* — Stoel Rives LLP

(57) ABSTRACT

Stent embodiments formed of a scaffolding structure are disclosed. Some embodiments may include a valve. A portion of the scaffolding structure may include a lattice structure formed by a plurality of interconnected arms arranged to form quadrilateral-shaped cells, such as diamond-shaped cells. The scaffolding structure may be formed by rows of strut arms arranged as annular segments and adjacent annular segments interconnected by connectors that extend in the longitudinal direction. The scaffolding structure may also be formed by rows of strut arms arranged in a helical pattern. The scaffolding structure has components configured to allow at least a portion of the stent to decrease in diameter in response to an axial force applied to the stent. Further, the components and elements of the stent may be configured to balance transverse forces applied to the stent, thus reducing the incidence of infolding.

11 Claims, 18 Drawing Sheets

(51) Int. Cl.
*A61F 2/915* (2013.01)
*A61F 2/04* (2013.01)

(52) U.S. Cl.
CPC ... *A61F 2002/044* (2013.01); *A61F 2220/005* (2013.01); *A61F 2220/0058* (2013.01); *A61F 2220/0075* (2013.01); *A61F 2230/0054* (2013.01)

(58) Field of Classification Search
CPC ........ A61F 2002/823; A61F 2/86; A61F 2/88; A61F 2/885; A61F 2/90; A61F 2/2418; A61F 2/915; A61F 2220/005; A61F 2220/0058; A61F 2220/0075
USPC .... 623/1.1, 1.12, 1.13, 1.14, 1.15, 1.16, 1.2, 623/1.21, 1.22, 1.24, 1.26, 1.3, 1.31, 1.34, 623/23.64, 23.7
See application file for complete search history.

(56) References Cited

U.S. PATENT DOCUMENTS

| | | |
|---|---|---|
| 5,314,473 A | 5/1994 | Godin |
| 5,607,445 A | 3/1997 | Summers |
| 5,662,713 A | 9/1997 | Andersen et al. |
| 5,766,263 A | 6/1998 | Grundei et al. |
| 5,827,321 A | 10/1998 | Roubin et al. |
| 5,833,707 A | 11/1998 | McIntyre et al. |
| 5,843,175 A | 12/1998 | Frantzen |
| 5,855,600 A | 1/1999 | Alt |
| 6,221,091 B1 | 4/2001 | Khosravi |
| 6,254,642 B1 | 7/2001 | Taylor |
| 6,264,700 B1 | 7/2001 | Kilcoyne et al. |
| 6,302,917 B1 | 10/2001 | Dua et al. |
| 6,348,065 B1 | 2/2002 | Brown et al. |
| 6,464,720 B2 | 10/2002 | Boatman et al. |
| 6,511,505 B2 | 1/2003 | Cox et al. |
| 6,544,291 B2 | 4/2003 | Taylor |
| 6,635,082 B1 | 10/2003 | Hossainy et al. |
| 6,669,724 B2 | 12/2003 | Park et al. |
| 6,701,174 B1 | 3/2004 | Krause et al. |
| 6,845,776 B2 | 1/2005 | Stack et al. |
| 6,878,162 B2 | 4/2005 | Bales et al. |
| 6,913,619 B2 | 7/2005 | Brown et al. |
| 6,929,658 B1 | 8/2005 | Freidberg et al. |
| 6,966,928 B2 | 11/2005 | Fell et al. |
| 6,991,647 B2 | 1/2006 | Jadhav |
| 7,182,788 B2 | 2/2007 | Jung |
| 7,462,192 B2 | 12/2008 | Norton et al. |
| 7,488,347 B1 | 2/2009 | Goble et al. |
| 7,547,321 B2 | 6/2009 | Silvestri et al. |
| 7,637,942 B2 | 12/2009 | Mangiardi et al. |
| 7,641,694 B1 | 1/2010 | Goble et al. |
| 7,695,446 B2 | 4/2010 | Levine et al. |
| 7,722,624 B2 | 5/2010 | Boucher et al. |
| 8,114,045 B2 | 2/2012 | Surti |
| 8,361,147 B2 | 1/2013 | Shterling et al. |
| 8,500,821 B2 | 8/2013 | Sobrino-Serrano et al. |
| 8,523,936 B2 | 9/2013 | Schmid et al. |
| 8,579,985 B2 | 11/2013 | Podolsky et al. |
| 8,632,600 B2 | 1/2014 | Zannis et al. |
| 8,986,368 B2 | 3/2015 | Gill et al. |
| 2002/0032479 A1 | 3/2002 | Hankh et al. |
| 2002/0068967 A1* | 6/2002 | Drasler et al. ............... 623/1.13 |
| 2002/0107565 A1 | 8/2002 | Greenhalgh |
| 2002/0116052 A1 | 8/2002 | Cox et al. |
| 2002/0138135 A1 | 9/2002 | Duerig et al. |
| 2003/0009236 A1 | 1/2003 | Godin |
| 2003/0060884 A1 | 3/2003 | Fell et al. |
| 2003/0109878 A1 | 6/2003 | Grundei |
| 2003/0220700 A1 | 11/2003 | Hammer et al. |
| 2004/0019374 A1 | 1/2004 | Hojeibane et al. |
| 2004/0044401 A1 | 3/2004 | Bales et al. |
| 2004/0068324 A1 | 4/2004 | Grundei |
| 2004/0088040 A1 | 5/2004 | Mangiardi et al. |
| 2004/0102866 A1 | 5/2004 | Harris et al. |
| 2004/0107004 A1 | 6/2004 | Levine et al. |
| 2004/0116996 A1 | 6/2004 | Freitag |
| 2004/0127973 A1* | 7/2004 | Mangiardi et al. .......... 623/1.15 |
| 2004/0204749 A1 | 10/2004 | Gunderson |
| 2004/0236424 A1 | 11/2004 | Berez et al. |
| 2004/0267350 A1 | 12/2004 | Roubin et al. |
| 2005/0033424 A1 | 2/2005 | Fell |
| 2005/0080491 A1 | 4/2005 | Levine et al. |
| 2005/0102038 A1 | 5/2005 | Grundei |
| 2005/0143745 A1 | 6/2005 | Hadorek et al. |
| 2005/0169893 A1 | 8/2005 | Koblish et al. |
| 2005/0183731 A1 | 8/2005 | Hunter et al. |
| 2006/0122686 A1 | 6/2006 | Gilad et al. |
| 2006/0122692 A1 | 6/2006 | Gilad et al. |
| 2006/0157543 A1 | 7/2006 | Abkowitz et al. |
| 2006/0212052 A1 | 9/2006 | Shin et al. |
| 2006/0253190 A1 | 11/2006 | Kuo |
| 2006/0259137 A1 | 11/2006 | Artof et al. |
| 2006/0276874 A1 | 12/2006 | Wilson et al. |
| 2007/0038290 A1 | 2/2007 | Huang et al. |
| 2007/0050011 A1 | 3/2007 | Klein et al. |
| 2007/0050021 A1 | 3/2007 | Johnson |
| 2007/0100437 A1 | 5/2007 | Welborn et al. |
| 2007/0112437 A1 | 5/2007 | Shank |
| 2007/0150049 A1 | 6/2007 | Nissl |
| 2007/0173946 A1 | 7/2007 | Bonutti |
| 2007/0198022 A1 | 8/2007 | Lang et al. |
| 2007/0198097 A1 | 8/2007 | Zegid |
| 2007/0239273 A1 | 10/2007 | Allen |
| 2007/0255412 A1 | 11/2007 | Hajaj et al. |
| 2007/0276463 A1 | 11/2007 | Nissl et al. |
| 2008/0004688 A1 | 1/2008 | Spenser et al. |
| 2008/0097579 A1 | 4/2008 | Shanley et al. |
| 2008/0132998 A1 | 6/2008 | Mangiardi et al. |
| 2008/0133020 A1 | 6/2008 | Blackwell et al. |
| 2008/0140181 A1 | 6/2008 | Reynolds et al. |
| 2008/0154351 A1 | 6/2008 | Leewood et al. |
| 2008/0200979 A1 | 8/2008 | Dieck et al. |
| 2008/0221664 A1* | 9/2008 | Bales et al. .................. 623/1.22 |
| 2008/0221670 A1 | 9/2008 | Clerc |
| 2008/0243225 A1 | 10/2008 | Satasiya et al. |
| 2008/0288044 A1 | 11/2008 | Osborne |
| 2009/0036976 A1* | 2/2009 | Beach et al. ................. 623/1.22 |
| 2009/0043373 A1* | 2/2009 | Arnault De La Menardiere et al. ............ 623/1.15 |
| 2009/0105809 A1 | 4/2009 | Lee et al. |
| 2009/0118830 A1 | 5/2009 | Fell |
| 2009/0171456 A1 | 7/2009 | Kveen et al. |
| 2009/0171465 A1 | 7/2009 | Bucay-Couto et al. |
| 2009/0187240 A1 | 7/2009 | Clerc |
| 2010/0004728 A1 | 1/2010 | Rao et al. |
| 2010/0036504 A1 | 2/2010 | Sobrino-Serrano et al. |
| 2010/0082093 A1 | 4/2010 | Weber |
| 2010/0114327 A1 | 5/2010 | Sobrino-Serrano |
| 2010/0121461 A1* | 5/2010 | Sobrino-Serrano et al. ........... 623/23.68 |
| 2010/0121462 A1 | 5/2010 | Sobrino-Serrano et al. |
| 2010/0137998 A1* | 6/2010 | Sobrino-Serrano et al. ........... 623/23.68 |
| 2010/0173066 A1 | 7/2010 | Mangiardi et al. |
| 2010/0256744 A1 | 10/2010 | Laborde et al. |
| 2010/0286760 A1* | 11/2010 | Beach et al. ................. 623/1.22 |
| 2011/0004290 A1 | 1/2011 | Bales, Jr. et al. |
| 2011/0054592 A1 | 3/2011 | Fliedner |
| 2011/0190874 A1 | 8/2011 | Celermajer et al. |
| 2011/0190905 A1 | 8/2011 | Behan |
| 2011/0265908 A1 | 11/2011 | Clerc |
| 2012/0010697 A1 | 1/2012 | Shin et al. |
| 2012/0059486 A1 | 3/2012 | Sobrino-Serrano et al. |
| 2012/0071987 A1 | 3/2012 | Levy |
| 2013/0006382 A1 | 1/2013 | Behan |

FOREIGN PATENT DOCUMENTS

| | | | |
|---|---|---|---|
| CN | 201500504 | 6/2010 | |
| EP | 1870057 | 12/2007 | |
| EP | 1870057 A1 * | 12/2007 | ............... A61F 2/06 |
| EP | 2329796 | 6/2011 | |

(56) References Cited

FOREIGN PATENT DOCUMENTS

| | | |
|---|---|---|
| EP | 2489331 | 8/2012 |
| WO | 2005089674 | 1/2005 |
| WO | 2005/089672 A1 | 9/2005 |
| WO | WO2005/089672 | 9/2005 |
| WO | 2006/047520 A2 | 5/2006 |
| WO | WO2006/047520 | 5/2006 |
| WO | 2006/069094 A1 | 6/2006 |
| WO | WO2006/069094 | 6/2006 |
| WO | 2009017827 | 2/2009 |
| WO | 2009085206 | 7/2009 |
| WO | 2009094188 | 7/2009 |
| WO | 2010024868 | 3/2010 |
| WO | WO2010/098857 | 9/2010 |
| WO | 2010124286 | 10/2010 |
| WO | WO2011/104269 | 9/2011 |
| WO | 2012035550 | 3/2012 |
| WO | WO2012/103501 | 8/2012 |

OTHER PUBLICATIONS

Office Action dated May 15, 2013 for U.S. Appl. No. 13/285,358.
Office Action dated Jan. 6, 2014 for U.S. Appl. No. 13/285,358.
International Search Report and Written Opinion dated Mar. 29, 2013 for PCT/US2012/060364.
Material Safety Data Sheet, © 2010 Polymer Systems Technology Limited™, UK & Ireland Distributor, NUSIL Silicone Technology. Effective Feb. 8, 2010, pp. 1-9.
International Search Report and Written Opinion dated Aug. 16, 2012 for PCT/US2012/035851.
Office Action dated Nov. 6, 2012 for U.S. Appl. No. 13/153,150.
Office Action dated Apr. 18, 2013 for U.S. Appl. No. 13/153,150.
Office Action dated Jan. 13, 2015 for U.S. Appl. No. 13/153,150.
Office Action dated Jan. 29, 2015 for U.S. Appl. No. 13/352,926.
European Search Report dated Feb. 18, 2015 for EP12793791.0.
Office Action dated Mar. 13, 2015 for U.S. Appl. No. 14/196,012.
International Search Report and Written Opinion dated May 15, 2014 for PCT/US2012/060364.
International Search Report and Written Opinion dated Jun. 10, 2014 for PCT/US2014/020187.
International Search Report and Written Opinion dated Jul. 1, 2014 for PCT/US2014/022328.
International Search Report and Written Opinion dated Sep. 13, 2013 for PCT/US2013/044013.
International Search Report and Written Opinion datedOct. 16, 2012 for PCT/US2012/060364.
Office Action dated Apr. 9, 2015 for U.S. Appl. No. 14/202,128.
Office Action dated Sep. 10, 2015 for U.S. Appl. No. 13/153,150.
Notice of Allowance dated Dec. 23, 2014 for U.S. Appl. No. 13/285,358.
Office Action dated Jun. 19, 2014 for U.S. Appl. No. 13/352,926.
Office Action dated Sep. 28, 2015 for U.S. Appl. No. 14/196,012.
European Search Report dated Jan. 27, 2016 for EP13801042.6.
Office Action dated Feb. 17, 2016 for U.S. Appl. No. 14/196,012.
Office Action dated Mar. 29, 2016 for U.S. Appl. No. 14/202,128.
Office Action dated Apr. 27, 2016 for U.S. Appl. No. 13/153,150.
Notice of Allowance dated Aug. 26, 2016 for U.S. Appl. No. 14/196,012.
Office Action dated Oct. 25, 2016 for U.S. Appl. No. 14/661,562.
Office Action dated Nov. 8, 2016 for U.S. Appl. No. 14/202,128.

* cited by examiner

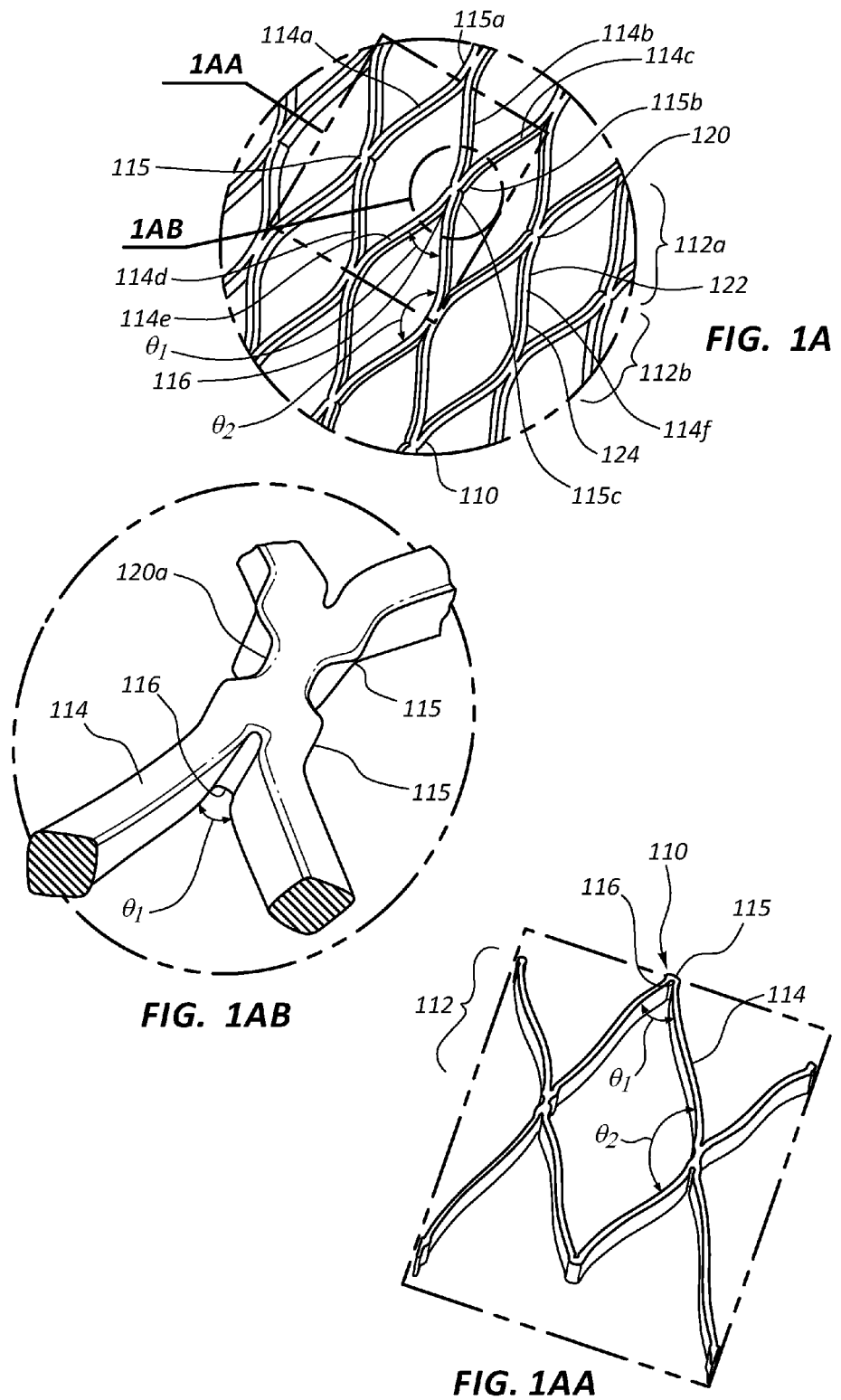

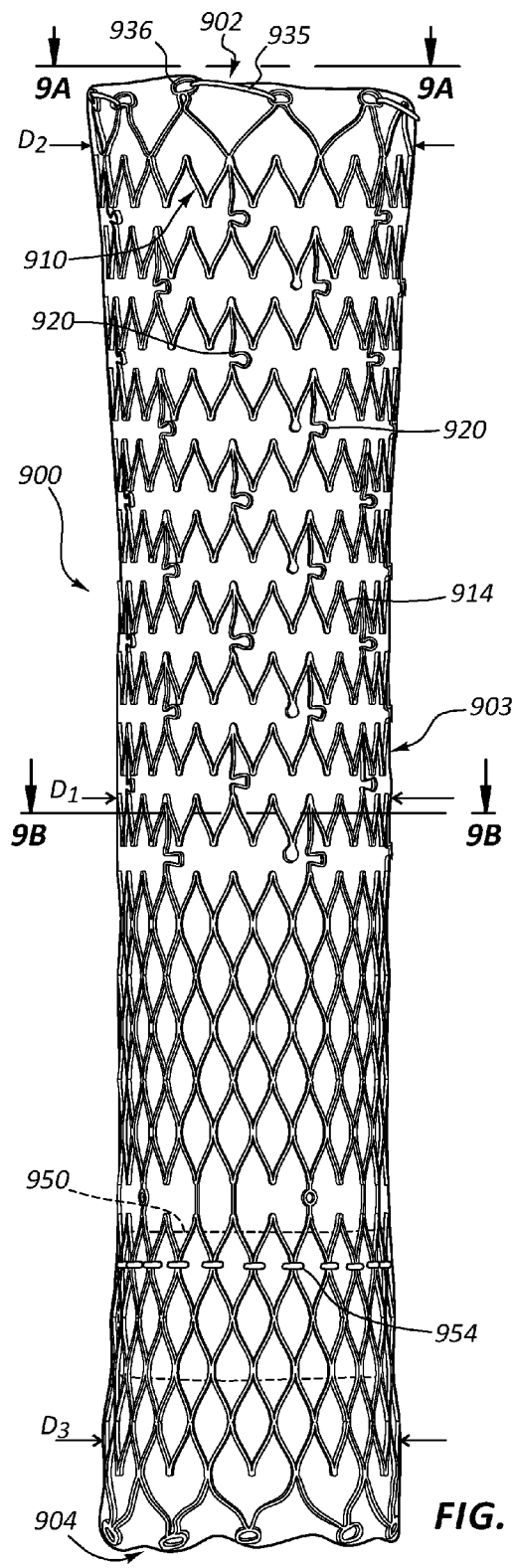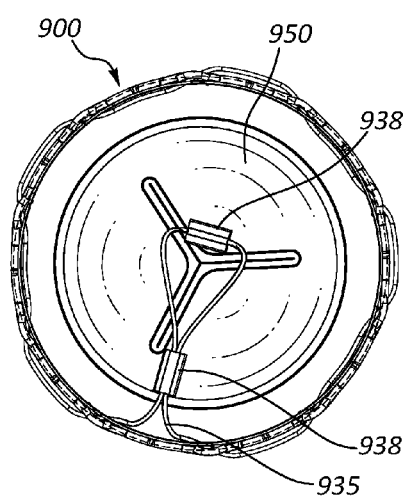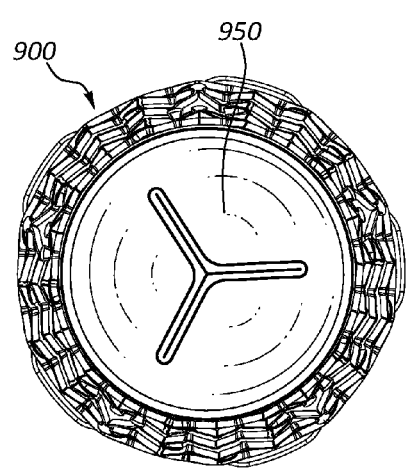
FIG. 9A
FIG. 9B
FIG. 9

ESOPHAGEAL STENT

CROSS-REFERENCE TO RELATED APPLICATIONS

This patent application claims priority to U.S. Provisional Patent Application No. 61/655,807 entitled ESOPHAGEAL STENT, filed on Jun. 5, 2012, which is incorporated herein by reference in its entirety.

TECHNICAL FIELD

The present disclosure relates generally to devices configured to be implanted within a body lumen. More particularly, the present disclosure relates to stents or similar prosthetic devices which, in certain embodiments, are configured to be disposed within the esophagus and which may comprise a valve.

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying drawings in which:

FIG. 1A is a close up view of a portion of the stent of FIG. 1.

FIG. 1AA is a further close up view of a portion of the stent of FIG. 1.

FIG. 1AB is a further close up view of a portion of the stent of FIG. 1.

FIG. 9 is a front view of another embodiment of a stent.

FIG. 9A is a top view of the stent of FIG. 9, taken through line 9A-9A.

FIG. 9B is a cross-sectional view of the stent of FIG. 9, taken through line 9B-9B.

FIG. 13 is a side view of an unexpanded stent in a "rolled out" state, depicted as if the stent were cut in the longitudinal direction and rolled out flat such that the entire circumference of the stent may be viewed flat.

DETAILED DESCRIPTION

Figure 1:
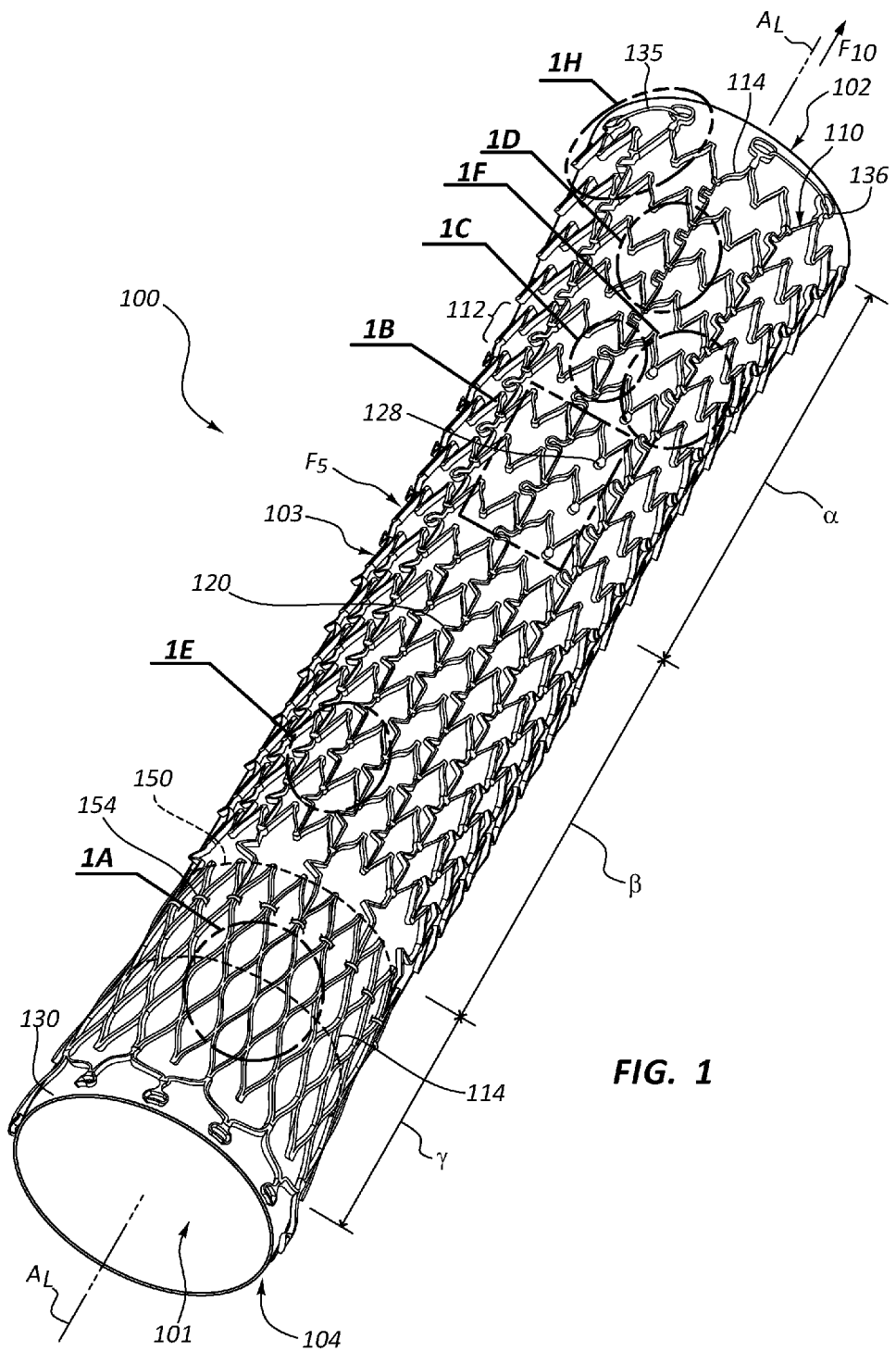
FIG. 1 is a perspective view of a stent, according to one embodiment of the present disclosure.

Implantable medical devices are useful tools of modern medicine. In general, an implantable device is a device or structure configured to be inserted or embedded into a patient and serves one or more of a variety of functions. Implantable devices include, for example, stents, filters, markers, drug delivery devices, valves, and monitors.

A stent is an implantable device that is inserted into a body lumen, such as a vessel or a passage, to keep the lumen open and prevent closure due to a stricture, external compression, or internal obstruction. Stents are commonly used to keep blood vessels open in the coronary arteries, and they are frequently inserted into the ureters to maintain drainage from the kidneys, the bile duct for pancreatic cancer or cholangiocarcinoma, or the esophagus or airways for strictures or cancer.

A stent may be configured with a support or scaffolding structure that may optionally be coupled to a cover. Additionally, the stent may comprise a variety of components, and the parameters of these components (e.g., shape, length, thickness, position, etc.) may be configured to provide a stent with certain properties. For example, the stent may be configured to distribute transverse loads or to change shape in response to certain forces. In some embodiments, the stent may also include a suture which may aid the user with repositioning or removal of the stent. Furthermore, the stent may comprise a valve which may be coupled to the inside diameter of the stent.

Though many of the examples provided herein refer to stents configured for use within the esophagus, the present disclosure is also applicable to a variety of stents designed for a variety of applications, such as biliary stents.

It will be readily understood with the aid of the present disclosure that the components of the embodiments, as generally described and illustrated in the figures herein, could be arranged and designed in a variety of configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

The phrases "connected to," "coupled to," and "in communication with" refer to any form of interaction between two or more entities, including mechanical, electrical, magnetic, electromagnetic, fluid, and thermal interaction. Two components may be coupled to each other even though they are not in direct contact with each other. For example, two components may be coupled to each other through an intermediate component.

The terms "proximal" and "distal" refer to opposite ends of a medical device. As used herein, the proximal end of a medical device is the end nearest a practitioner during use, while the distal end is the opposite end. For example, the proximal end of a stent refers to the end nearest the practitioner when the stent is disposed within, or being deployed from, a deployment device. For consistency throughout, these terms remain constant in the case of a deployed stent, regardless of the orientation of the stent within the body. In the case of an esophageal stent—deployed through the mouth of a patient—the proximal end will be nearer the head of the patient and the distal end nearer the stomach when the stent is in a deployed position.

FIG. 1 is a perspective view of one embodiment of a stent 100. As shown in the illustrated embodiment, the stent 100 may comprise a scaffolding structure 110 comprised of a plurality of strut arms 114. The scaffolding structure 110 may define a generally cylindrical shape that has a proximal end 102, a distal end 104, and a lumen 101 formed through the generally cylindrical shape of the scaffolding structure 110. The lumen 101 may extend in the longitudinal direction (a direction along the longitudinal axis $A_L$) between the proximal end 102 and the distal end 104. The scaffolding structure 110 may further comprise a cover 130 coupled to the scaffolding structure 110, a suture 135, and a valve 150.

The scaffolding structure 110 may comprise any suitable material known in the art, including plastics and memory alloys. In some embodiments, the scaffolding structure 110 may be constructed of nitinol, including ASTM F2063. The thickness of the scaffolding structure 110 may be between about 0.30 mm and about 0.60 mm. In other embodiments, the thickness of the scaffolding structure 110 may be between about 0.35 mm and about 0.55 mm. In other embodiments, the thickness of the scaffolding structure 110 may be between about 0.40 mm and about 0.50 mm. In other embodiments, the thickness of the scaffolding structure 110 may be about 0.47 mm.

As illustrated in FIG. 1, the scaffolding structure 110 may be formed of multiple annular segments 112 (or rings) disposed on a circumference and defining at least a portion of the generally cylindrical shape of the scaffolding structure 110. Each annular segment 112 may comprise a plurality of interconnected strut arms 114. For example, the strut arms 114 may be connected such that they form a zigzag pattern, defining alternating "peaks" and "valleys," around the annular segment 112. (As used herein, "peaks" refer to the relative high points and "valleys" refer to the relative low points where strut arms 114 arranged in a zigzag pattern connect. In other words, the peaks and valleys may be relative to one end 102, 104 of the stent 100, rather than relative to the circumference of the stent 100.) In some embodiments adjacent strut arms 114 may form acute angles relative to each other.

In some embodiments, adjacent annular segments 112 may be arranged in rows around a longitudinal axis $A_L$ of the generally cylindrical shape of the scaffolding structure 110. The rows may be arranged in the longitudinal direction of the generally cylindrical shape of the scaffolding structure 110. Adjacent annular segments 112 may be coupled to each other by connectors 120. In some embodiments, adjacent annular segments 112 may be interconnected by a plurality of connectors 120 to form diamond-shaped cells. In some embodiments, adjacent annular segments 112 may be interconnected by a plurality of connectors 120 to form a lattice structure. In some embodiments, the lattice structure may comprise and/or define diamond-shaped cells.

In some embodiments, adjacent annular segments 112 may abut and be coupled to one another to form diamond-shaped cells without the use of connectors 120. In some embodiments, adjacent annular segments 112 may abut and be interconnected to one another to form a lattice structure without the use of connectors 120.

In some embodiments, adjacent annular segments 112 may be interconnected to form cells that are shaped different than diamond-shaped cells. For example, in some embodiments, adjacent annular segments 112 may be interconnected to form irregularly shaped cells. In some embodiments, adjacent annular segments 112 may be interconnected to form cells that are non-quadrilateral in shape.

The stent 100 may further be configured with a valve 150. In some embodiments, such as the embodiment of FIG. 1, the valve 150 may be coupled to an inside diameter of the stent 100. Thus, the valve 150 is not directly visible in the illustration of FIG. 1, though its position is indicated by a reference line. A suture 154 may be used to secure the valve 150 to an inner diameter of the stent 100. For example, the suture 154 may secure the valve 150 to strut arms 114 of the scaffolding structure 110 of the stent 100. In another embodiment, the suture 154 may secure the valve 150 to the cover 130 of the stent 100. In another embodiment, a plurality of ties may be used to secure the valve 150 to an inner diameter of the stent 100.

In some embodiments, the stent 100 may be divided into one or more zones along the longitudinal length of the stent 100. For example, the stent 100 shown in FIG. 1 may be separated into three longitudinal zones or segments: a proximal zone α; a transition zone β; and a valve zone γ. The stent 100 may be configured such that different segments or zones of the stent have different structural or geometric features or components. The stent 100 may also be configured such that different segments or zones have different physical properties. For example, the stent 100 may be designed such that different zones have a different hoop force and crush force.

As used herein, hoop force refers to the magnitude of a radial force applied around the circumference and toward a center longitudinal axis $A_L$ of the stent 100 that causes the stent 100 to collapse. Accordingly, a stent with a relatively high hoop force may be more resistant to collapse when compared to a stent with a relatively low hoop force. A stent designed with a low hoop force may therefore be easier to sheath or recapture.

As used herein, crush force refers to the magnitude of a two-dimensional force (e.g., pinch force) applied on the stent 100 in a transverse direction with respect to the center longitudinal axis $A_L$ that causes the stent 100 to deform. Accordingly, a stent with a relatively high crush force may be more resistant to deformation by strictures or other physiological features when compared to a stent with a relatively low crush force.

In some embodiments, the stent 100 may be configured with one or more zones that have a relatively low hoop force and a relatively high crush force. The one or more zones may allow the stent 100 to be easily sheathed or recaptured and may also be capable of resisting deformation by strictures or other physiological structures. In other embodiments, the stent 100 may be configured with one or more zones that have hoop force and crush force that each are relatively high or relatively low. In other embodiments, the stent 100 may be designed such that the hoop force and crush force vary between and/or within each zone of the stent 100.

In some embodiments, the stent 100 may be designed such that one or more zones may be relatively "soft" (e.g., more easily compressible, or less resistant to compression or deformation, in a transverse direction). As used herein, the term "soft" refers to areas with relatively low hoop force and relatively low crush force. In some applications, the relative softness of a particular zone, for example the proximal zone α, may be configured to cause less trauma to tissue that contacts the stent 100 when implanted. Further, a stent 100 designed with a soft proximal end 102 (or a soft proximal zone α) may be more easily removed or repositioned.

Analogously, a stent 100 may be designed with one or more zones that are relatively "stiff" (e.g., less easily compressible, or more resistant to compression or deformation, in a transverse direction). As used herein, the term "stiff" refers to areas with relatively high hoop force and relatively high crush force. The relative stiffness of a particular zone may provide additional structure and support to prevent deformation and/or collapse of the stent 100. For example, the stiffness of a particular zone, for example the valve zone γ, may resist deformation by strictures or other physiologic features or conditions at a therapy site. The stiffness of, for example, the valve zone γ may also protect a valve of the stent 100 from deformation and/or damage.

In some embodiments, the stent 100 may be configured with relatively soft and relatively stiff zones in order to tailor the stent 100 to a specific therapy. For example, designing the stent 100 with relatively soft ends may result in relatively less discomfort, or pain, caused by contact of the stent ends with body tissue. Thus, in some embodiments the portion of the stent 100 configured to be implanted at the treatment location may be relatively stiff—allowing it to resist stricture and otherwise function as part of a desired treatment—while other portions are relatively soft to reduce trauma and pain at those points.

A stent 100 comprising diamond-shaped cells may be designed to have a relatively low hoop force when compared to stents 100 that do not comprise diamond-shaped cells. Additionally, a stent 100 comprising diamond-shaped cells may have a relatively high crush force. In certain embodiments, such as the embodiment illustrated in FIG. 1, the stent 100 may be designed such that the strut arms 114 of adjacent annular segments 112 are interconnected to form diamond-shaped cells in the valve zone γ. In other embodiments, the stent may be designed such that the strut arms 114 of adjacent annular segments 112 are interconnected to form diamond-shaped cells in the valve zone γ and transition zone β (see e.g., FIG. 2). In some embodiments, the stent may be designed such that the strut arms 114 of adjacent annular segments 112 are interconnected to form diamond-shaped cells in the valve zone γ, the transition zone β, and the proximal zone α (see e.g., FIG. 3). Accordingly, the strut arms 114 of adjacent annular segments 112 may be interconnected to form diamond-shaped cells within any zone.

FIG. 1A is a close up view of a portion of the scaffolding structure 110 of FIG. 1 wherein adjacent strut arms 114a, 114b, 114c of an annular segment 112a are interconnected to form a zigzag pattern of alternating "peaks" and "valleys."

For example, adjacent strut arms 114a and 114b are interconnected such that they form a "peak" at apex 115a, and strut arms 114b and 114c are interconnected such that they form a "valley" at apex 115b. Throughout this disclosure, particular examples of components may be designated by a letter following the reference numeral. For example, reference number 114 refers generally to the strut arms of the scaffolding structure 100. Specific strut arms 114, such as those illustrated in FIG. 1A, are labeled 114a, 114b and 114c. This pattern of identifying particular examples of general or repeating components may be used throughout this disclosure.

FIG. 1AA is a further close up view of the scaffolding structure 110 shown in FIG. 1A depicting adjacent strut arms 114 within an annular segment 112 coupled at an apex 115. The angle $\theta_1$ formed at the apexes 115 by two adjacent strut arms 114 within an annular segment 112 may be designed to provide the stent 100 with particular properties. For example, in embodiments wherein adjacent annular segments 112 are aligned and interconnected to form diamond-shaped cells, the angle $\theta_1$ formed at each apex 115 may be from about 15 degrees to about 45 degrees. In some embodiments, the angle $\theta_1$ formed at each apex 115 may be from about 20 degrees to about 40 degrees. In some embodiments, the angle $\theta_1$ formed at each apex 115 may be from about 20 degrees to about 35 degrees. In some embodiments, the angle $\theta_1$ formed at each apex 115 may be from about 20 degrees to about 30 degrees. In some embodiments, the angle $\theta_1$ formed at each apex 115 may be about 25 degrees.

In embodiments wherein adjacent annular segments 112 are aligned and interconnected to form irregular shaped cells that are non-quadrilateral in shape, the angle $\theta_1$ formed at each apex 115 may be between about 25 degrees to about 55 degrees. In some embodiments, the angle $\theta_1$ formed at each apex 115 may be from about 35 degrees to about 50 degrees. In some embodiments, the angle $\theta_1$ formed at each apex 115 may be from about 40 degrees to about 50 degrees. In some embodiments, the angle $\theta_1$ formed at each apex 115 may be about 45 degrees.

As discussed in more detail below, apex angles $\theta_1$ within the aforementioned ranges may be configured to aid with balancing one or more compressive forces, such as force $F_5$, applied in transverse direction inward towards the center longitudinal axis $A_L$ of the stent 100 to prevent infolding of the stent.

As used herein, infolding refers to inward protrusions or wrinkles that may form along the inside diameter of a stent in response to unbalanced transverse compressive forces on the stent. For example, an esophageal stent may infold as a result of the peristaltic motion of the esophagus. In other instances, a stent may infold due to forces exerted by an uneven portion of the body lumen, such as a stricture or buildup of scar tissue.

As used herein, transverse forces are forces acting in the transverse direction of the stent 100. Transverse forces may be compressive such that a force may be exerted toward the center longitudinal axis $A_L$ of the stent 100, such as the direction of force $F_5$ shown in FIG. 1. Alternatively, transverse forces may refer to an expansion force exerted in a radial outward direction from the center longitudinal axis $A_L$ (e.g., opposite the direction of force $F_5$). A stent designed to generally balance transverse compressive forces may tend to resist infolding. In other words, a stent may have compressive forces applied unevenly in different transverse directions. The design of the stent may be configured to transfer these forces such that the stent distributes the load more evenly around the circumference of the stent. In particular, the angles $\theta_1$ between adjacent strut arms 114 may be configured to transfer uneven loads, further allowing the stent 100 to resist infolding.

In some embodiments, such as the embodiment of FIG. 1AB, the inner surface of the apex 115 may be substantially circular or semi-circular in shape, forming an inner radius 116. The inner radius 116 of the apex 115 may be sized so as to impart particular characteristics to the stent 100. For example, the radius 116 may be large as compared to the angle $\theta_1$ formed by the two inner surfaces of the coupled strut arms 114. In such instances, the inner surfaces of the strut arms 114 and the radius 116 may form a rough "keyhole" shape. In other embodiments, the radius 116 and strut arms 114 may not form a keyhole shape, though the radius 116 is still relatively large. Designs that incorporate relatively large radii 116 may provide desired characteristics to the stent 100, such as surface finish, fatigue life, and fracture resistance. The size of the radius 116 may vary depending on the desired properties of the stent 100. In some embodiments, the radius 116 may be from about 15 microns to about 95 microns. In some embodiments, the radius 116 may be from about 30 microns to about 80 microns. In some embodiments, the radius 116 may be from about 45 microns to about 65 microns.

Moreover, in certain embodiments, the stent 100 may be designed with different radii 116 in different portions of the stent 100. In some embodiments, for example, the geometric features of certain zones may impact the size of the radii 116 within that zone. In embodiments wherein adjacent annular segments 112 are aligned and interconnected to form diamond-shaped cells, the number of diamond cells around the circumference of the stent 100 may impact the size of the radii 116. For example, in portions of the stent 100 with relatively more diamond-shaped cells around the circumference of the stent 100, less material may be available to allow for large radii 116. Accordingly, embodiments with about 14 diamond-shaped cells around the circumference of the stent 100 may allow for relatively larger radii 116; embodiments with about 22 diamond-shaped cells around the circumference of the stent 100 may allow for relatively smaller radii 116; and embodiments with about 18 diamond-shaped cells around the circumference of the stent 100 may allow for radii 116 that have a size between the size of the radii 116 of embodiments with about 14 and about 22 diamond-shaped cells around the circumference of the stent 100.

In embodiments wherein adjacent annular segments 112 are aligned and interconnected to form irregular shaped cells that are non-quadrilateral in shape, the number of connectors 120 may impact the size of the radii 166. For example, in portions of the stent 100 with relatively more connectors 120, less material may be available to allow for large radii 116. In one embodiment, a stent 100 may be designed such that the radii are from about 40 microns to about 60 microns, including radii of about 54 microns, in portions of the stent 100 with about 5 connectors 120 around the circumference of the stent 100. Similarly, portions of the stent 100 with about 10 connectors 120 around the circumference of the stent 100 may have radii 116 from about 25 microns to about 45 microns, including radii of about 35 microns. Finally, portions of the stent 100 with about 20 connectors 120 around the circumference of the stent 100 may have smaller radii 116, such as from about 10 microns to about 20 microns, including radii of about 15 microns. It will be appreciated by one of skill in the art having the benefit of this disclosure that these values may vary in differing designs; for example, a stent 100 may be cut with a relatively large number of connectors 120, but with relatively narrow connectors 120 to allow more material for larger radii 116.

The geometry of the strut arms 114 may be modified to provide the stent 100 with particular properties. For example, each strut arm 114 may define a length along the strut arm 114. Again, as shown in both FIG. 1 and FIG. 1A, each strut arm 114 within an annular segment 112 is coupled to at least two other strut arms 114 within the annular segment 112, forming apexes 115 on both ends of the strut arm 114. The length of a single strut arm 114 is the length of the strut arm 114 from a first end to a second end, or the distance between each apex 115 at which the strut arm 114 is coupled to an adjacent strut arm 114. A wide variety of strut arm 114 lengths is within the scope of this disclosure. For example, in embodiments wherein adjacent annular segments 112 are aligned and interconnected to form diamond-shaped cells, the strut arms 114 may have a length between about 4.5 mm and about 12 mm. In other embodiments, the strut arms 114 may have a length between about 6 mm and about 10 mm. In other embodiments, the strut arms 114 may have a length of about 9 mm.

In embodiments wherein adjacent annular segments 112 are aligned and interconnected to form irregular shaped cells that are non-quadrilateral in shape, the strut arms 114 may have a length of between about 4 mm and about 5.25 mm. In some embodiments, the strut arms 114 may have a length of between about 4.25 mm and about 5.0 mm. In some embodiments, the strut arms 114 may have a length of between about 4.5 mm and about 4.75 mm.

The relative lengths of the strut arms 114 may affect the overall properties of the stent 100. For instance, the portions of the stent 100 that have relatively longer strut arms 114 may be "softer" (again, meaning more compressible in a transverse direction) than portions of the stent 100 where the strut arms 114 are relatively shorter.

In some embodiments, the strut arms 114 in the annular segments 112 that are positioned adjacent the distal 104 and proximal 102 ends may be relatively longer than strut arms 114 in annular segments 112 near the mid-body 103 of the stent 100. Thus, the stent 100 may be stiffer, or less compressible in a transverse direction, at the inner portions of the proximal zone α, as compared to the portion of the zone adjacent the proximal end 102 of the stent 100. In other embodiments, a stent 100 may be designed with strut arms of uniform length throughout, of a particular length along certain portions of the stent (for example, near both the proximal end 102 and mid-body 103), or of varying lengths along the entire stent 100. Further, in some embodiments, the strut arms 114 may have a length that is substantially constant for all the strut arms 114 located on the same annular segment 112. In other embodiments, the strut arms 114 may have a length that varies within one or more individual annular segments 112.

In still other embodiments, the stent 100 may be designed such that the strut arm 114 lengths in a particular zone of the stent 100 are constant and gradually change in other zones. For instance, in some embodiments, a relatively long stent may be formed by forming a mid-body 103 section with a constant strut arm length and gradually increasing the strut arm length in sections adjacent the ends 102, 104 of the stent 100. Numerous stent lengths are within the scope of this disclosure, including, for example, stents from about 70 mm and about 150 mm in length, including stents from about 100 mm and about 120 mm in length.

In certain embodiments, the strut arms 114 may be curved. A strut arm 114f illustrated in FIG. 1A, for example, may be understood as having a first portion 122 and a second portion 124. The first portion 122 and the second portion 124 may or may not be the same length. The strut arm 114f may be generally formed with an inflection point located between the first portion 122 and the second portion 124 of the strut arm 114f. Thus, in the illustrated embodiment, the strut arm 114f may be curved in the general shape of a sigmoid curve. In other words, the first portion 122 of the strut arm 114f forms a first roughly arcuate path, and the second portion 124 of the strut arm 114f forms a second roughly arcuate path. In the illustrated embodiment, the center of the first arcuate path is on the opposite side of the arm than the center of the second arcuate path. Thus, the strut arm 114f has a wave-like shape formed by the strut arm 114f starting to curve in one direction, and then curving in a second direction. Accordingly, strut arm 114f has an "inflection point" at or around the point where the first portion 122 meets the second portion 124. In the embodiment of FIG. 1, each strut arm 114 is shaped substantially as described in connection with strut arm 114f.

In other embodiments, the strut arms 114 may be substantially straight, or may resemble other types of curves. Furthermore, while in some instances each strut arm 114 may have a curved shape similar to the other strut arms 114 on the stent 100, in other embodiments multiple strut arms 114 may have different shapes, including strut arms 114 disposed in the same annular segment 112.

In some embodiments, one or more adjacent annular segments 112 may be coupled by one or more connectors 120. As shown in FIG. 1A, in some embodiments, the connector 120 couples the two adjacent annular segments 112a, 112b by coupling a valley apex 115b of the annular segment 112a to the peak apex 115c of the annular segment 112b. In some embodiments, a stent may be designed such that the peaks of an annular segment are circumferentially aligned with the valleys of an adjacent annular segment, such as annular segments 112a and 112b. In other embodiments, the peaks and valleys of adjacent annular segments may be circumferentially offset.

In the embodiment of FIG. 1, the peaks of each annular segment 112 in the valve zone γ are approximately circumferentially aligned with the valleys of adjacent annular segments 112 in the valve zone γ, whereas the peaks of each annular segment 112 in the transition zone β and proximal zone α are approximately circumferentially aligned with the peaks of adjacent annular segments 112 in the transition zone β and proximal zone α, respectively. As will be appreciated by one of skill in the art having the benefit of this disclosure, in alternative embodiments any combination of alignment/non-alignment of peaks and valleys between any set of annular segments is within the scope of this disclosure, regardless of the zone.

In some embodiments, circumferentially aligned peaks and valleys of adjacent annular segments 112 may be interconnected by one or more connectors 120 to form diamond-shape cells. For example, as shown in FIG. 1A, strut arms 114a and 114b of annular segment 112a may be connected to strut arms 114d and 114e of annular segment 112b such that the four strut arms 114a, 114b, 114d, 114e form a diamond-shaped cell, or other quadrilateral shape (e.g., rhombus, parallelogram, rectangle, and square). The quadrilateral shape may have substantially parallel opposing sides. The apexes of neighboring annular segments 112 may be integrally connected and/or formed. In other embodiments, adjacent annular segments 112 are not interconnected by one or more connectors 120 to form diamond-shaped cells. In some embodiments, a plurality of annular segments 112 may be arranged and interconnected by connectors 120 to form a lattice structure. In some embodiments, the lattice structure may comprise and/or form substantially diamond-shaped cells.

In embodiments wherein adjacent annular segments 112 are aligned and interconnected to form diamond-shaped cells, the angles (e.g., $\theta_1$, $\theta_2$) within the diamond-shaped cells may vary. Each diamond-shaped cell contains four inner angles, angle $\theta_1$, angle $\theta_2$, and the angles opposite angle $\theta_1$, and angle $\theta_2$. As previously discussed, the degree of angle $\theta_1$ may vary depending on the desired properties of the stent 100. Moreover, in some embodiments, angle $\theta_1$ and the angle opposite $\theta_1$ may be substantially the same. In other embodiments, angle $\theta_1$ and the angle opposite $\theta_1$ may differ. Similarly, in some embodiments, angle $\theta_2$ and the angle opposite $\theta_2$ may be substantially the same; and in other embodiments, angle $\theta_2$ and the angle opposite $\theta_2$ may differ. In some embodiments, each of the four angles within a diamond-shaped cell may vary depending on the length and height of the diamond-shaped cell.

The length of a diamond-shaped cell formed by adjacent interconnected annular segments 112 may vary depending on the length of the individual strut arms 114 and/or on the angle(s) (e.g., angles $\theta_1$, $\theta_2$) between adjacent strut arms 114. In some embodiments, the length of the diamond-shaped cells (i.e., the length of the diamond-shaped cell between the top peak and the bottom peak along the longitudinal axis $A_L$) may range from about 8 mm to about 24 mm. In other embodiments, the length of the diamond-shaped cells may range from about 11 mm to about 20 mm. In other embodiments, the length of the diamond-shaped cells may range from about 14 mm to about 18 mm.

As discussed above with respect to the length of the individual strut arms 114, the length of the diamond-shaped cells may affect the characteristics of the stent 100. For example, portions of the stent 100 comprising relatively longer diamond-shaped cells may be "softer" (again, meaning more compressible in a transverse direction) than portions of the stent 100 comprising relatively shorter diamond-shaped cells. Accordingly, portions of the stent 100 comprising relatively longer diamond-shaped cells may have lower hoop force and be easier to sheath or recapture than portions of the stent 100 comprising relatively shorter diamond-shaped cells. Portions of a stent 100 comprising diamond-shaped cells that are relatively shorter in length may be designed to be stiffer and have higher hoop force and crush force as compared to areas of a stent 100 comprising diamond-shaped cells that are relatively longer in length.

The size and shape of the connectors 120 may vary depending on the desired characteristics of the stent 100. In some embodiments, the connectors 120 may be relatively short such that the apexes 115 of annular segments 112 may, in essence, abut one another. In other embodiments, the connectors 120 may be relatively longer and extend for some distance in the longitudinal direction of the stent 100 such that there may be a distance between adjacent annular segments 112. In embodiments wherein adjacent annular segments 112 are aligned and interconnected to form diamond-shaped cells, the length of the connectors 120 may range from about 0.25 mm to about 4 mm. In other embodiments, the length of the connectors 120 may range from about 0.50 mm to about 3.5 mm. In other embodiments, the length of the connectors 120 may range from about 1 mm to about 2.5 mm. In other embodiments, the length of the connectors 120 may range from about 1.25 mm to about 1.75 mm.

In embodiments wherein adjacent annular segments 112 are aligned and interconnected to form irregular shaped cells that are non-quadrilateral in shape, the length of the connectors 120 may range from about 4.25 mm to about 12 mm. In other embodiments, the length of the connectors 120 may range from about 5 mm to about 10 mm.

In embodiments wherein peaks and valleys (or valleys and peaks) of adjacent annular segments 112 are aligned and interconnected to form irregular shaped cells that are non-quadrilateral in shape, the length of the connectors 120 may range from about 4.25 mm to about 7.5 mm. In other embodiments, the length of the connectors 120 may range from about 5 mm to about 6.5 mm. In other embodiments, the length of the connectors 120 may range from about 5.25 mm to about 5.5 mm.

In embodiments wherein peaks and peaks (or valleys and valleys) of adjacent annular segments 112 are aligned and interconnected to form irregular shaped cells that are non-quadrilateral in shape, the length of the connectors 120 may range from about 8 mm to about 12 mm. In other embodiments, the length of the connectors 120 may range from about 8.5 mm to about 11 mm. In other embodiments, the length of the connectors 120 may range from about 9 mm to about 9.5 mm.

As shown in the embodiment of FIG. 1AB, the connector 120a may have a "neck down" shape. In other words, the width of the connector 120a may be smaller than the width of the apexes 115 to which the connector 120a is coupled. Connectors 120a having a "neck down" shape may add flexibility and/or elasticity to the stent 100. Alternatively, in some embodiments, the connector 120 may not be necked down; rather, the width of the connector 120 may be the same as the width of the apexes 115 to which the connector 120 is coupled.

Figure 1B:
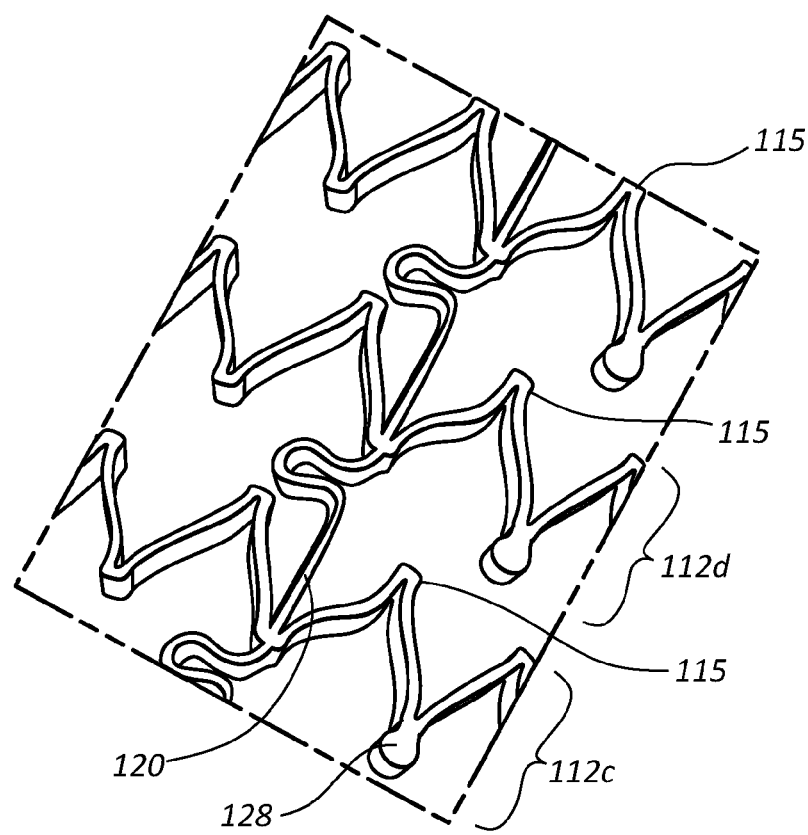
FIG. 1B is a second close up view of a portion of the stent of FIG. 1.

At the portion of the stent 100 shown in FIG. 1B, the adjacent annular segments 112c, 112d are aligned such that apexes 115 at the peak of the zigzag pattern in the annular segment 112c are circumferentially aligned with apexes 115 at the peak of the zigzag pattern of the adjacent annular segment 112d. In other words, the peak apexes 115 and valley apexes 115 of adjacent annular segments 112c, 112d may be said to be circumferentially offset. The connectors 120 that span between a peak and a peak or a valley and a valley may be configured to impart more flexibility to the stent 100 than relatively shorter peak to valley connectors 120 or valley to peak connectors 120.

Figure 1C:
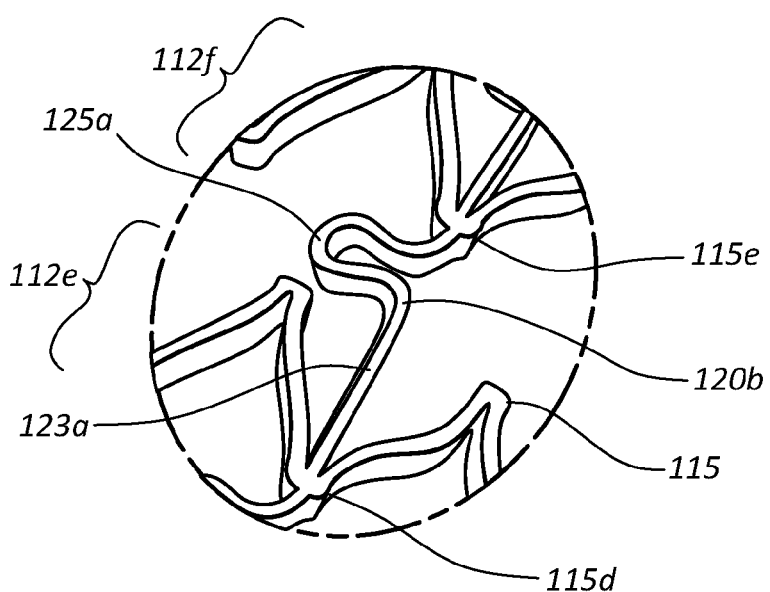
FIG. 1C is a third close up view of a portion of the stent of FIG. 1.

FIG. 1C is a close up view of a portion of the proximal zone α of the stent 100 of FIG. 1, showing a particular connector 120b. The connector 120b couples two adjacent annular segments 112e, 112f together, and is coupled to each annular segment 112e, 112f at apexes 115d, 115e on each annular segment 112e, 112f. Connector 120b has a first portion 123a and a second portion 125a. In the illustrated embodiment, the first portion 123a is relatively straight and spans much of the distance between the adjacent annular segments 112. In other embodiments, the first portion 123a may be more or less curved than the first portion 123a of the illustrated embodiment. The second portion 125a may be substantially formed in a rounded shape, in some instances forming the general profile of the symbol omega (Ω). In some embodiments, the omega-shaped second portion 125a may add axial strength to the stent 100. In some instances, axial strength may be desirable for repositioning or removing a stent 100.

Further, in some embodiments, omega-shaped connectors 120 may add flexibility and/or elasticity to the stent 100. The omega shape, having two ends relatively near each other connected by a relatively long curved member (the round portion of the omega) may be configured to provide added flexibility to the stent 100. The other connectors 120 within the proximal zone α of the stent 100 may be generally shaped like the connector 120b disclosed above. It is within the scope of this disclosure, however, to use any type or shape of connector 120 at any point along the stent 100.

Figure 1D:
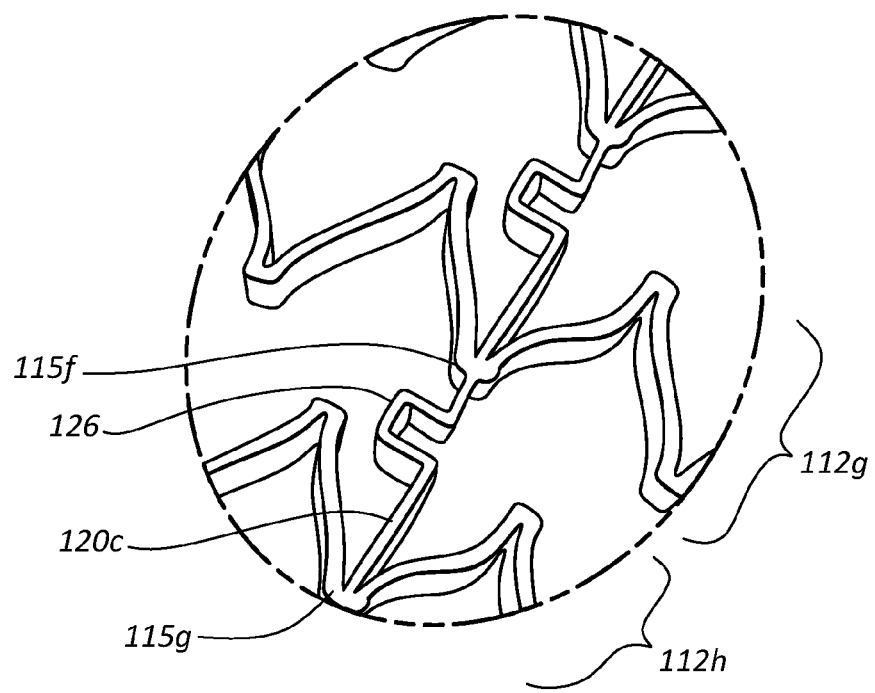
FIG. 1D is a fourth close up view of a portion of the stent of FIG. 1.

FIG. 1D is a close up view of a portion of the proximal zone α of the stent 100 of FIG. 1, showing a particular connector 120c. In the illustrated embodiment, annular segments 112g and 112h are coupled to a connector 120c at apex 115f and apex 115g, respectively. Connector 120c extends between each apex 115f, 115g and includes a generally U-shaped or square portion 126 located near the center of the connector 120c. As with the omega-shaped connectors 120 disclosed above, it is within the scope of this disclosure to use a connector 120 with a square portion 126, such as connector 120c of FIG. 1D, at any point along the stent 100.

Figure 1E:
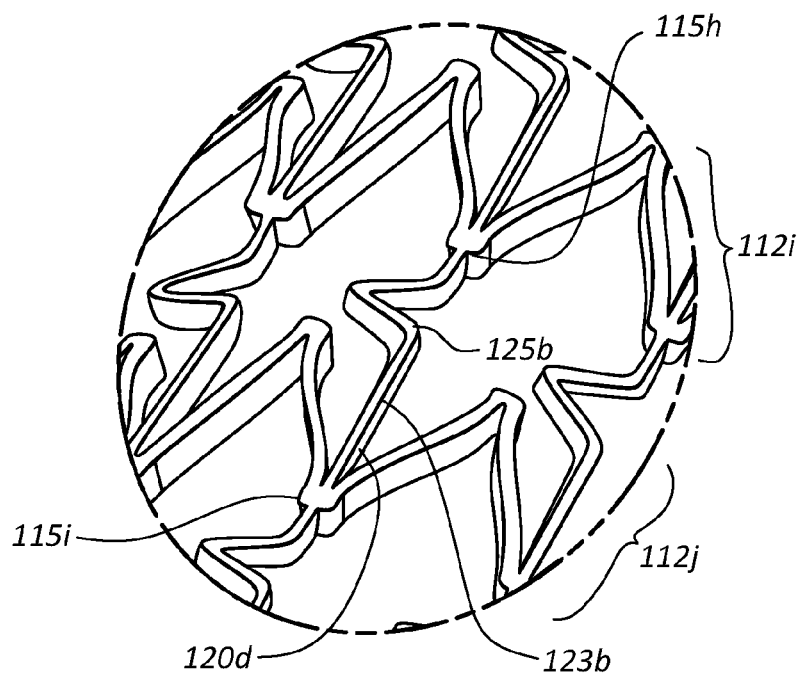
FIG. 1E is a fifth close up view of a portion of the stent of FIG. 1.

FIG. 1E is a close up view of a portion of the transition zone β of the stent 100 of FIG. 1, showing a particular connector 120d. Similar to the connector 120b of FIG. 1C, the connector 120d couples two adjacent annular segments 112i, 112j together, and is coupled to each annular segment 112i, 112j at apexes 115h, 115i on each annular segment 112i, 112j. Again, similar to the connector 120b of FIG. 1C, the connector 120d has a first portion 123b and a second portion 125b. In the illustrated embodiment, the first portion 123b is relatively straight and spans much of the distance between the adjacent annular segments 112i, 112j. In other embodiments, the first portion 123b may be more or less curved than the first portion 123b of the illustrated embodiment. The second portion 125b may be substantially formed in a V-shape. As with the omega-and square shaped connectors 120 disclosed above, it is within the scope of this disclosure to use a connector 120 with a V-shaped second portion 125b, such as connector 120d of FIG. 1E, at any point along the stent 100.

In some embodiments, V-shaped connectors may be used in place of, or in connection with, omega-shaped connectors as described above. V-shaped connectors may be used in place of omega-shaped connectors in applications where the additional axial strength provided by omega-shaped connectors is not necessary; for example, in the embodiment of FIG. 1 the axial strength provided by twenty total connectors per annular segment may obviate the need for omega-shaped connectors for some applications. Further, V-shaped connectors may reduce the force required to crimp a stent for loading into a catheter.

Additionally, the shape of the connectors 120 may be influenced by the surrounding geometry of the stent 100. For example, the gap between adjacent annular segments 112 and the total number of connectors 120 per annular segment 112 may limit the amount of material available to be shaped into a connector 120. In some embodiments, for example, omega-shaped connectors 120 (which require relatively more material) may not be feasible in zones with a large number, such as 20, of connectors 120 per annular segment 112. V-shaped connectors 120 (which require relatively less material) may be more feasible in such zones.

In the embodiment of FIG. 1, omega- and square-shaped connectors 120 are utilized in the proximal zone α of the stent 100. It is within the scope of this disclosure to use any shape of connector 120 within any zone, or to use multiple shapes of connectors 120 within the same zone. Additional types and shapes of connectors 120 known in the art may also be utilized in the present disclosure. It is therefore within the scope of this disclosure to use any type or shape of connector 120 at any point along the stent 100.

Additionally, as shown in the illustrated embodiment of FIG. 1, in some embodiments, connectors 120 may interconnect peaks and valleys (or peaks and peaks, or valleys and valleys, etc.) that are aligned along the longitudinal direction of the stent 100. In other embodiments, however, connectors 120 may interconnect peaks and valleys (or peaks and peaks, or valleys and valleys, etc.) that are not aligned along the longitudinal direction of the stent 100. Accordingly, in some embodiments, connectors 120 may be curved, sigmoid shaped, or relatively "S" shaped, and may couple peaks and valleys (or peaks and peaks, or valleys and valleys, etc.) that are not aligned along the longitudinal direction of the stent 100.

The number of connectors 120 per annular segment 112 may vary depending on the design of the stent 100. Furthermore, in certain embodiments, a stent 100 may be configured with different numbers of connectors 120 per annular segment 112, along the length of the stent 100. For example, the number of connectors 120 included in a particular zone may be configured to affect the properties of the stent 100 in that zone. In the embodiment of FIG. 1, for instance, the stent 100 has more connectors 120 per annular segment 112 in the valve zone γ than in the transition zone β, and more connectors 120 per annular segment 112 in the transition zone β than in the proximal zone α.

Accordingly, in different embodiments, the number of connectors 120 associated with any annular segment 112 may vary. In embodiments wherein adjacent annular segments 112 are aligned and interconnected to form diamond-shaped cells, the number of connectors may vary between about 14 to about 22. In some embodiments, there may be between about 16 to about 20 connectors 120 per annular segment 112. In some embodiments, there may about 18 connectors 120 per annular segment 112. In embodiments wherein adjacent annular segments 112 are aligned and interconnected to form irregular shaped cells that are non-quadrilateral in shape, there may be about 4 to about 20 connectors 120 per annular segment 112. In other embodiments, the absolute number of connectors in each zone may vary from these values, as may the ratio of connectors 120 per annular segment 112 in each zone.

In some embodiments, the proximal-most row of the proximal zone α, may be configured with about 10 or more connectors 120 to provide more uniform crimping as compared to sections of the stent 100 with only about 5 connectors 120 per annular segment 112. In other embodiments, the stent 100 may be configured with the same number (5, 10, or some other number) of connectors per annular segment 112 throughout the entire proximal zone α.

In embodiments wherein the stent 100 has more connectors 120 at the proximal-most end than the rest of the proximal zone α, the greater number of connectors 120 may be configured for a number of functions. For example, a greater number of connectors 120 at the proximal end may be configured to add resiliency and strength to the end of the stent 100. In particular, in embodiments where the ends of the stent flare out to relatively large diameters, additional connectors 120 may add strength to minimize the potential for infolding at the oversized end. Additionally, a larger number of connectors 120 may be configured to provide for more uniform crimping of the stent in preparation for loading the stent into a catheter, and for more uniform expansion upon deployment. In some embodiments a stent 100 may have additional connectors 120 associated with more than one row near the proximal end 102. For example, the first 1, 2, 3, 4, 5, or more proximal-most annular segments may be configured with additional connectors 120.

In some embodiments, the connectors 120 of adjacent annular segments 112 may be aligned in the circumferential direction along the longitudinal direction of the stent 100. In other embodiments, the connectors 120 may be offset circumferentially along the longitudinal direction of the stent 100, or aligned, along any longitudinal segment of the stent 100.

In some embodiments, the connectors 120 linking the first 3 annular segments 112, beginning with the proximal-most annular segment 112, may be offset circumferentially from each other. This alternating alignment of the connectors 120, as well as the thickness of the scaffolding structure 110, may be configured to enable the stent 100 to resist infolding. For example, in some instances the alternating alignment of the connectors 120 may tend to localize stent deformation caused by strictures in the lumen of the patient, rather than transferring such deformations along the length of the stent 100. In some embodiments, the connectors 120 may be offset at one or both ends of the stent 100 due to increased concern for infolding at the ends of the stent 100. This may be particularly true in stents 100 with flared ends, which have a more open (and therefore softer) scaffolding structure 110 near the ends. While some embodiments may have alternating connectors 120 associated with the 3 proximal-most annular segments 112; other embodiments may have more or fewer annular segments 112 with alternating connectors 120, including 1, 2, 3, 4, 5, or 6 annular segments 112.

As with varying the lengths of strut arms 114, described above, variations in the number of connectors 120 per annular segment 112 may affect the relative stiffness of the stent 100. Generally, portions of the stent 100 with a larger number of connectors 120 per annular segment 112 may be relatively stiffer than portions with fewer connectors 120. The relative stiffness of different portions may not be constant, however, due to other factors such as strut arm 114 length, as discussed above.

The total number of strut arms 114 on each annular segment 112 around the circumference of stent 100 may vary depending on the design of the stent 100, and may be influenced by the geometry of the stent 100; for example, the number of connectors 120, strut arm width, and size of the inside radii 116 may all impact the total number of strut arms 114 which may be disposed about the circumference of the stent 100. Similarly, the desired angle $\theta_1$ of each apex 115 may impact the number of strut arms 114 which may be disposed about the circumference of the stent 100. For example, in embodiments wherein adjacent annular segments 112 are aligned and interconnected to form diamond-shaped cells, for apex angles $\theta_1$ of about 15 degrees to about 45 degrees, there may be between about 14 to about 22 diamond-shaped cells arranged around the circumference. In embodiments with apex angles $\theta_1$ of about 20 degrees to about 30 degrees, there may be between about 17 to about 19 diamond-shaped cells arranged around the circumference. In embodiments with apex angles $\theta_1$ of about 25 degrees, there may be between about 18 diamond-shaped cells arranged around the circumference. In embodiments wherein adjacent annular segments 112 are aligned and interconnected to form irregular shaped cells that are non-quadrilateral in shape, for apex angles $\theta_1$ of between about 25 degrees to about 55 degrees, there may be between about 16 and about 24 pairs of strut arms 114 disposed about the circumference. For apex angles $\theta_1$ of between about 35 degrees and 50 degrees, there may be between about 18 and about 22 pairs of strut arms 114 disposed about the circumference. In some embodiments configured for apex angles $\theta_1$ of about 45 degrees, there may be about 20 pairs of strut arms 114 about the circumference. In some embodiments, any of these parameters, including the number of strut arms 114 and apex angle $\theta_1$, may vary in different zones of the same stent 100.

The number of diamond-shaped cells formed by adjacent annular segments 112 arranged around the circumference of the stent 100 may be modified depending on the desired properties of the stent 100. For example, increasing the number of diamond-shaped cells arranged around a given circumference may provide the stent 100 with higher hoop force and crush force. In some embodiments, the number of diamond-shaped cells arranged around a given circumference will affect the inner angles (e.g., $\theta_1$ $\theta_2$) of the diamond-shaped cells. A stent 100 having a circumference about between about 19 mm and about 23 mm may have between about 14 to about 22 diamond-shaped cells arranged around its circumference. In other embodiments, the number of diamond-shaped cells arranged around the circumference of the stent 100 may be from about 16 to about 20. In other embodiments, the number of diamond-shaped cells arranged around the circumference of the stent 100 may be from about 17 to about 19. In other embodiments, the number of diamond-shaped cells arranged around the circumference of the stent 100 may be about 18.

Figure 1F:
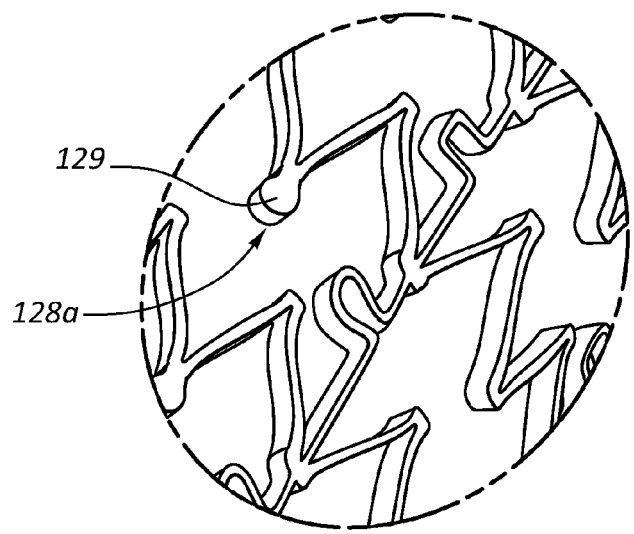
FIG. 1F is a sixth close up view of a portion of the stent of FIG. 1.

The stent 100 of FIG. 1 further includes generally rounded anti-migration portions 128 coupled to certain apexes 115 within the proximal zone α. FIGS. 1B and 1F show close up views of anti-migration portions 128, including anti-migration portion 128a of FIG. 1F. In some embodiments, the anti-migration portion 128a may be configured to contact portions of the inside diameter of a body lumen, and thus restrict migration of the stent 100 within the body lumen. The rounded head 129 of the anti-migration portion 128a, may be from about 0.75 mm in diameter to about 1.5 mm in diameter. In some embodiments, the diameter of the rounded head 129 of the anti-migration portion 128a may be from about 1.0 mm to about 1.3 mm. In some embodiments, the diameter of the rounded head 129 of the anti-migration portion 128a may about 1.2 mm.

Figure 1G:
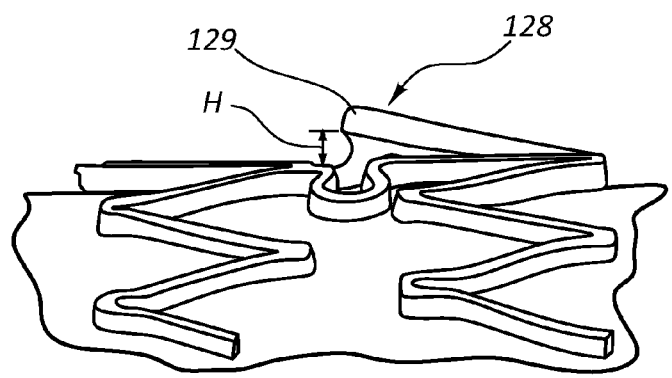
FIG. 1G is a side view of the portion of the stent of FIG. 1F.

FIG. 1G shows a side view of the stent of FIG. 1F. As depicted in FIG. 1G, in certain embodiments, the anti-migration portions 128 may be positioned such that the rounded head 129 is displaced outward from the outside diameter of the stent 100. For example, the anti-migration portions 128 may be positioned such that the distance H that the rounded head 129 is displaced outward from the outside diameter of the stent 100 may be between about 0.1 mm to about 0.9 mm. In some embodiments, the distance H may be between about 0.3 mm to about 0.7 mm. In some embodiments, the distance H may be about 0.5 mm. This arrangement may allow the anti-migration portion 128 to engage the body lumen and minimize migration of the stent 100. In some embodiments, each anti-migration portion 128 may be disposed outwardly, though in other embodiments not every anti-migration portion may be so disposed.

The total number of anti-migration portions 128 may vary depending on the size of the stent 100 and the application for which it is configured. For example, an esophageal stent having a length of about 100 mm may include from about 15 to about 25 anti-migration portions, including about 20 total anti-migration portions. Similarly, an esophageal stent having a length of about 120 mm may include from about 25 to 35 anti-migration portions, including about 30 total anti-migration portions, and an esophageal stent having a length of about 150 mm may include from about 35 to 45 anti-migration portions, including about 40 anti-migration portions.

In the embodiment of FIG. 1, each anti-migration portion 128 is disposed in a distally oriented direction, thus configured to minimize migration of the stent 100 in the distal direction. In the case of an esophageal stent, such a design may be configured to counteract the peristaltic forces of the esophagus. In other embodiments, some or all of the anti-migration portions 128 may likewise be disposed in the proximally oriented direction to minimize migration of the stent 100 in the proximal direction.

The stent 100 of FIG. 1 further includes a cover 130 coupled to the scaffolding structure 110, the cover 130 defining an inner portion of the stent 100. The cover 130 may be elastomeric, polymeric, or comprised of any other material known in the art. In some embodiments, the cover may include silicone, while in certain embodiments the cover may be comprised only of silicone.

In some embodiments, the cover 130 may be applied such that it tends to ebb and flow into spaces between portions of the scaffolding structure 110 of a stent, resulting in a "tire tread" like outer surface, rather than a smooth outer cover. In some embodiments such a design may be configured to allow tissue to lock into the uneven spaces and treads, thus adding anti-migration properties in some instances.

In some embodiments the cover 130 may include multiple subparts or layers. For example, in some embodiments the cover 130 may be a two-part design. Such two-part covers may be composed of a base cover which encapsulates the scaffolding structure 110 and a second cover which may be applied after the first cover cures. In certain embodiments, the second cover may only be applied to the outside diameter of the stent 100 and may chemically bond to the first cover layer. For example, a stent may have a cover with a first layer comprised of a medical grade silicone such as TSP-8021, and a second layer, applied to the outside diameter of a particularly low friction silicone, such as Nusil MED-6670. In other embodiments, the second layer may comprise parylene. Multiple layered covers may be configured such that the primary layer adds elasticity or resiliency to the stent while the second, outer layer reduces friction along the outside diameter. It is within the scope of this disclosure to use any of the exemplary materials for any of the layers.

In embodiments which utilize a particularly low friction cover 130 on the outside diameter of the stent 100, the outer cover may be configured to more easily allow the stent to be loaded into a catheter and/or to decrease the catheter size necessary to sheath the stent 100. Specifically, a low friction outer layer, such as Nusil MED-6670 disclosed above, may reduce the coefficient of friction between a catheter and a stent by as much as 50% in some applications.

Further, an additional lubricant, such as Nusil MED-400, for example, may be utilized to increase the ergonomics of the system, allowing the stent 100 to be more easily loaded into, or deployed from, a catheter. In some embodiments, silicone lubricants may be used, including fluorinated polymers such as MED-400. Use of fluorination may reduce the solubility of the lubricant in some silicone elastomers; thus use of a fluorinated lubricant may reduce the tendency of the lubrication to dissolve into the silicone base over time.

Figure 1H:
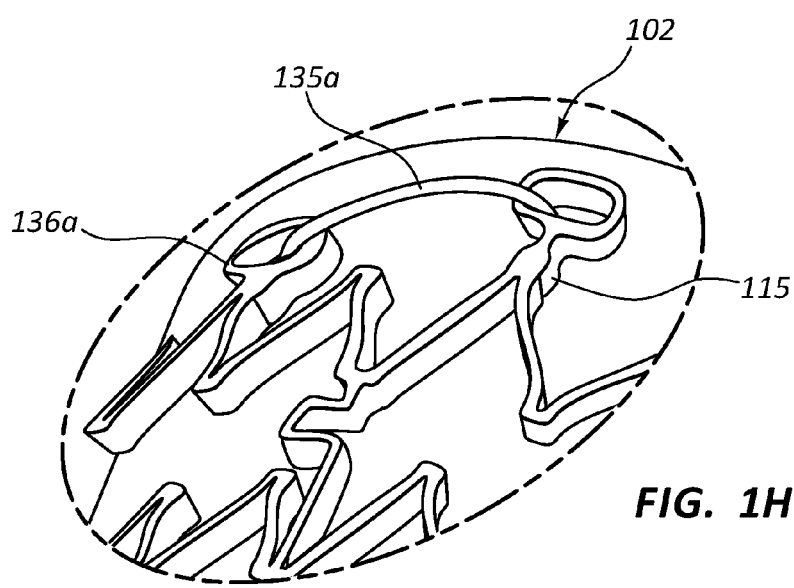
FIG. 1H is a seventh close up view of a portion of the stent of FIG. 1.

FIG. 1H is a close up view of the proximal end 102 of an embodiment of the stent 100 of FIG. 1. As shown in FIGS. 1 and 1H, the stent 100 may include suture threading eyelets 136a or apertures, coupled to one or more apexes 115 of the scaffolding structure 110 at the proximal end 102 of the stent 100. The suture threading eyelets 136a may be configured to receive a suture 135a and couple it to the stent 100. In other embodiments the stent 100 may also or alternatively comprise a suture (not shown) disposed adjacent the distal end 104 of the stent 100.

Furthermore, the suture threading eyelets 136 may be elongated in the circumferential direction of the stent 100. Such a design may be configured to distribute the expansive force of a stent 100 acting on a body lumen when the stent 100 is deployed. This distribution of force, in connection with the smooth and rounded shape of the eyelets 136, may be configured to lessen the trauma to body tissue which contacts the end 102 of the stent 100.

The suture threading eyelets 136 may be configured to locate the suture 135 substantially at the proximal end 102 of the stent 100. In other words, the eyelets 136 may be positioned such that the entire scaffolding structure 110 is located distal of the eyelets 136. Such positioning may be configured to create a relatively uniform purse string effect when the suture 135 is engaged. Thus, in some embodiments, the uniformity of the purse string effect may be influenced by the proximity of the suture threading eyelets 136 to the proximal end 102 of the stent 100. In other embodiments, the uniformity of the purse string effect may instead, or also, be due to the elongated nature of the eyelets 136 which may allow a suture 135 to more readily slide through the eyelets 136 during tightening.

In some ways analogous to the eyelets 136 at the proximal end 102, the stent 100 may be configured with rounded elongate knobs coupled to one or more apexes 115 of the scaffolding structure 110 at the distal end 104 of the stent 100. In some aspects these knobs may resemble the shape of the eyelets 136 though there is no hole present in the knobs. Further, the knobs may be larger or smaller than eyelets 136 on the same stent 100, depending on stent design parameters, such as the relative size and flare of the proximal 102 and distal 104 ends of the stent 100.

Similar to the eyelets, the elongated design of the knobs may be configured to distribute the expansive force of a stent 100 acting on a body lumen when the stent 100 is deployed. This distribution of force, in connection with the smooth and rounded shape of the knobs, may be configured to lessen the trauma to body tissue which contacts the distal end 104 of the stent 100.

The relative size of the suture threading eyelets 136 may be related to the total number of eyelets 136 and the diameter of the tube of material from which the stent 100 is cut. In some embodiments, the eyelets 136 may be shaped with the maximum elongation in the circumferential direction, or a direction around the longitudinal axis $A_L$, allowed by the number of eyelets 136 and the circumference of the tube. Similarly, in some embodiments the rounded elongate knobs may be sized as large as possible given the diameter of the material from which the stent 100 is formed. Again referring to the illustrated embodiment, adjacent knobs and/or eyelets 136 may be offset along the longitudinal direction in order to allow for relatively larger knobs and/or eyelets 136. In other embodiments the knobs and/or eyelets 136 may all be in-line or may be disposed at more than two longitudinal positions.

The features and elements of the stent 100 of FIG. 1 may be configured to create a stent with particular characteristics and features. In addition to the disclosure recited above, the disclosure provided hereinafter—in connection with any figure or discussion—is equally relevant to controlling the characteristics of a finished stent. Any part of the present disclosure may be combined with any other part of the disclosure to configure a stent. Thus, while certain aspects or parameters—for example, strut arm length or flared ends—may be discussed in connection with one embodiment, such disclosure is relevant to all embodiments.

A stent with substantially the geometry and features described in connection with the stent 100 of FIG. 1 may be configured to "neck down" in response to an axial force, such as force $F_{10}$, applied in a direction along the longitudinal axis $A_L$ away from the proximal end of the stent 100. In other words, the diameter of the stent 100 may be reduced (e.g., stent 100 may be partially collapsed) by applying an axial force $F_{10}$ to the proximal end of the stent 100 in the longitudinal direction away from the stent 100. Similarly, the diameter of the stent 100 may also be reduced by applying an axial force to the distal end of the stent 100 in the longitudinal direction opposite force $F_{10}$ and away from the stent 100. In some embodiments, various portions of the stent 100 may be in contact with the body lumen thereby creating forces that may act against an axial force $F_{10}$ applied to the stent 100. Necking down may occur as the axial force $F_{10}$ is increased relative to any forces acting against the axial force $F_{10}$. Necking down may be used in connection with removing or repositioning a deployed stent. The decrease in diameter may pull the stent 100 out of contact with the body lumen, allowing a practitioner to displace the stent 100 while avoiding some trauma to the body lumen.

Additionally, portions of the stent near the suture may neck down as an axial force, such as force $F_{10}$ is applied in the longitudinal direction of the stent, in some instances the stent necking down to a diameter which is less than the mid-body of the stent. In some embodiments, a stent may be configured such that a force of about 2 pounds causes the stent to neck down as described.

In some instances this necking down may occur near the ends of the stent 100, including instances where the stent 100 only necks down at one end of the stent. For example, a practitioner may reposition the stent 100 within a body lumen or remove the stent 100 from the body lumen by first engaging a suture 135 located near one end of the stent. At the suture location the stent 100 may decrease in diameter as force is applied to the suture 135; in other words the stent may contract or "purse string" as the suture 135 is tightened. In some embodiments the force associated with this purse string effect may be understood as a compressive force acting around the circumference of the stent 100 at the suture location.

In certain embodiments a stent may be configured to decrease in size, due to one or both of the purse string effect and necking down, primarily at the ends of the stent. In some instances, tissue granulation or other tissue ingrowth into the stent may occur primarily at the ends of the stent. Thus, some stents may be configured to decrease in diameter at the ends to allow a practitioner to dislodge the stent ends from the wall of the body lumen, including in cases where there is tissue granulation at the ends of the stent.

As stated above, each of the elements described above may be manipulated to control the necking down characteristics of a stent. In particular, a stent such as stent 100 of FIG. 1 may neck down due to the elasticity of the cover 130, the thickness of the scaffolding structure 110, and the configuration of the geometry at the ends 102 and 104 of the stent 100, including the inclusion of suture eyelets, and the circumferentially alternating arrangement of certain connectors. A stent such as stent 100 may neck down as much as 50% in response to an axial force in the longitudinal direction of the stent.

A practitioner may begin the process of repositioning or removing a stent, such as stent 100, by first engaging the sutures. The sutures may be used to compress one end such that the end is pulled away from the lumen wall. The practitioner may then apply an axial force in the longitudinal direction to the end of the stent, causing a portion of the stent to neck down and pull away from the lumen wall. The practitioner may then reposition or remove the stent with minimal trauma to the body lumen.

In some embodiments, a stent may be crimped and packed within a catheter by a manufacturer, prior to shipping. In other embodiments, a stent may be self-sheathing (see e.g., FIG. 10). As used herein, a "self-sheathing" stent is a stent configured to be at least partially sheathed by a user, either in the context of initially sheathing a stent (for example prior to deployment) or in the context of sheathing a deployed stent for repositioning or removal. Thus, in some embodiments, a stent may be configured such that the self-sheathing process does not deform or alter the stent in such a way as to limit the usability of the stent when subsequently deployed. In some embodiments, a self-sheathed stent may be configured such that a user may sheath the stent just prior to use. For embodiments which utilize a valve, a stent may be configured to be, at least partially, self-sheathing to avoid deforming the valve for an extended period of time. For example, a stent with a valve when crimped and packed in a catheter for an extended period of time, may kink, crease, or otherwise plastically deform. Thus, in some embodiments, a stent may be designed such that it is partially or fully self-sheathing, minimizing the time the valve is deformed within a catheter. Specifically, in some embodiments a stent may be designed such that a portion of the stent is crimped and loaded by a manufacturer, while the portion of the stent containing the valve is sheathed by the user just prior to use.

Certain features of the stent 100 may be configured to allow the stent to be self-sheathing. A stent 100 may be configured such that a portion of the proximal zone α is crimped and sheathed within a catheter prior to use. Circumferentially aligned connectors 120 along portions of the proximal zone α, transition zone β, and valve zone γ which are not pre-loaded into the catheter may be configured to provide axial strength to the stent 100, allowing the remainder of the stent to be pulled into a catheter by the user without the stent 100 deforming in the axial direction. A deployment device may be configured to anchor to the stent at one or more points along the stent wherein the connectors 120 are circumferentially aligned. In some embodiments, a stent 100 may have circumferentially aligned connectors 120 along the entire length of the stent 100. In still other embodiments, all the connectors 120 may be offset, or aligned in some zones and offset in other zones. In some instances, deployment devices may be utilized, which are configured to grip the stent 100 at any point. Aligned connectors 120 may be optional in such embodiments.

In some embodiments, interconnecting adjacent annular segments 112 to form diamond-shaped cells in at least the valve zone γ may aid in self loading of the stent 100. A stent 100 comprising diamond-shaped cells may be designed to have lower hoop forces as compared to stents 100 that do not comprise diamond-shaped cells. Moreover, a stent 100 comprising diamond-shaped cells may still maintain acceptable crush forces. In some embodiments, strut arms 114 arranged and interconnected to form diamond-shaped cell patterns may create a self-funnel when being sheathed into a catheter by the practitioner. Adjacent annular segments 112 arranged and interconnected to form diamond-shaped cell patterns may also create less friction between the stent 100 and the catheter during self loading as annular segments 112 arranged and interconnected to form the diamond-shaped cell pattern may more easily slide into a catheter as compared to annular segments 112 connected by an omega, square or V-shaped connector 120 where the catheter may become caught on the outward portion of the omega, square, or V-shape.

In some embodiments, interconnecting the strut arms 114 to form diamond-shaped cells in the stent 100 may allow a practitioner to re-capture the stent 100 up to a pre-determined point. For example, a practitioner may deploy 30 mm of stent and may not like how the procedure is proceeding and then may re-capture the stent into the catheter during the procedure.

The transition zone β may be configured such that the transition between the proximal zone α and the valve zone γ is not overly extreme. The transition zone β may be configured such that the axial and radial forces required for self-sheathing are uniformly transferred between the proximal zone α and the valve zone γ of the stent 100. Furthermore, the transition zone β may be configured to provide uniform expansion between the proximal zone α and valve zone γ during deployment of the stent 100.

In the embodiment of FIG. 1, no anti-migration portions 128 are located within the valve zone γ or the transition zone β. Thus, in the illustrated embodiment, all anti-migration portions 128 may be crimped and loaded into the catheter by a manufacturer, minimizing the chance of the anti-migration portions 128 catching on the edge of the catheter, or otherwise interfering with self-sheathing. In other embodiments anti-migration portions 128 may be positioned at any point along the stent 100, including portions that are configured for self-sheathing. In some embodiments, disposing the anti-migration portions 128 in a distally oriented direction may aid in self sheathing by minimizing the change of the anti-migration portions 128 catching on the edge of the catheter, or otherwise interfering with self-sheathing.

Figures 2, 2A:
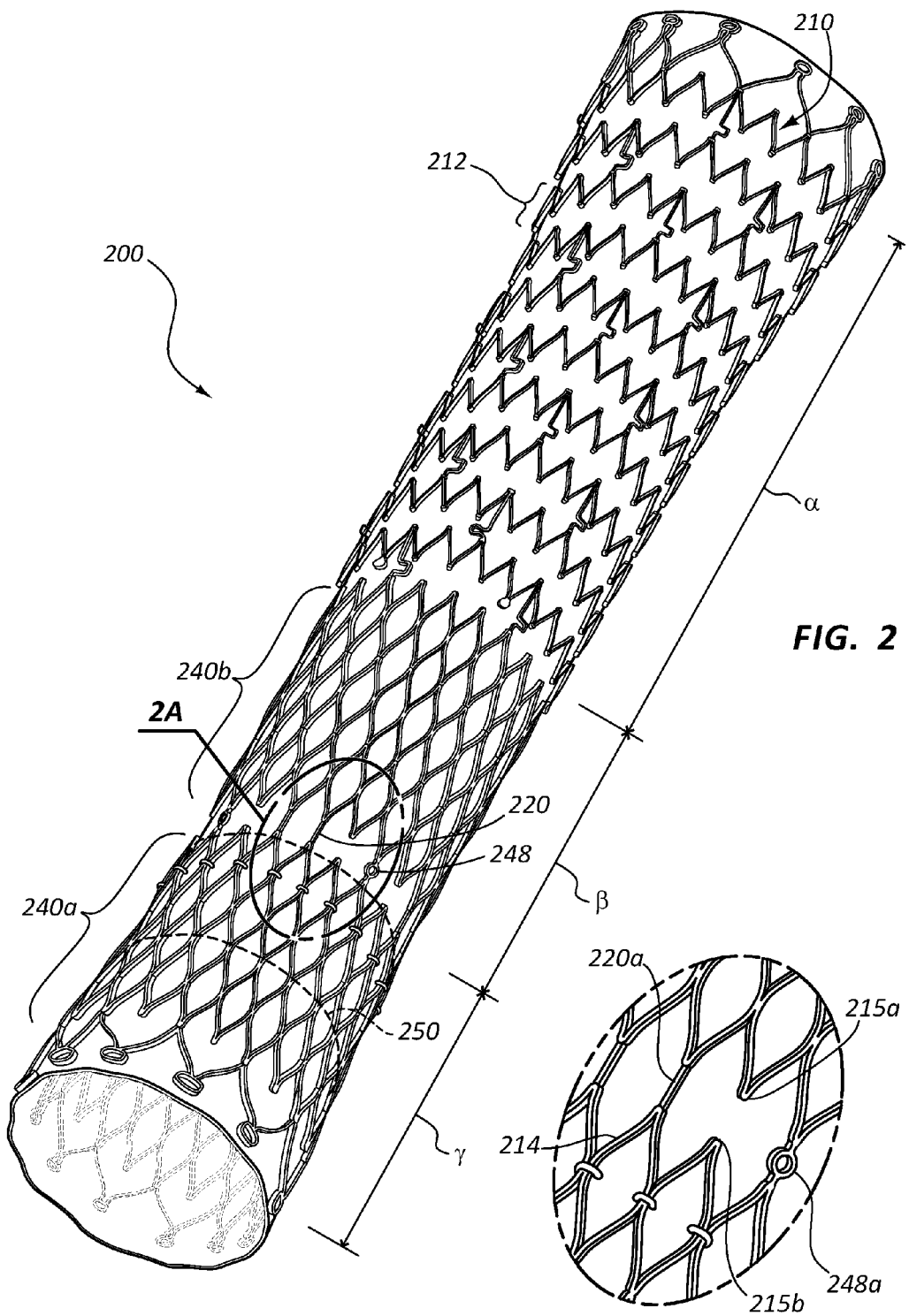
FIG. 2 is a perspective view of another embodiment of a stent.
FIG. 2A is a close up view of a portion of the stent of FIG. 2.

FIG. 2 is a perspective view of another embodiment of a stent 200 wherein a plurality of adjacent annular segments 212 are aligned and interconnected such that lattice structures are formed in the valve zone γ and transition zone β. Stent 200 can, in certain respects, resemble components of the stent described in connection with FIGS. 1 and 1A-1H above. It will be appreciated that all the illustrated embodiments may have analogous features. Accordingly, like features are designated with like reference numerals, with the leading digits incremented to "2." (For instance, the stent is designated "100" in FIG. 1, and an analogous stent is designated as "200" in FIG. 2.) Relevant disclosure set forth above regarding similarly identified features thus may not be repeated hereafter. Moreover, specific features of the stent and related components shown in FIG. 2 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the stent of FIG. 2. Any suitable combination of the features, and variations of the same, described with respect to the stent 100 and components illustrated in FIGS. 1 and 1A-1H, can be employed with the stent 200 and components of FIG. 2, and vice versa. This pattern of disclosure applies equally to further embodiments depicted in subsequent figures and described hereafter.

As illustrated in FIG. 2, in some embodiments, the stent 200 may comprise a plurality of annular segments 212 aligned and interconnected such that they form lattice structures 240a, 240b in the valve zone γ and transition zone β, respectively. The proximal zone α may also comprise a lattice structure. Each lattice structure 240a, 240b is disposed on a circumference and defines at least a portion of the generally cylindrical shape of the scaffolding structure 210. Moreover, the lattice structures 240a, 240b are arranged along a longitudinal direction of the generally cylindrical shape of the scaffolding structure 210. In the illustrated embodiment of FIG. 2, the lattice structures 240a, 240b may comprise and/or define substantially diamond-shaped cells.

As shown in FIGS. 2 and 2A, connectors 220 interconnect adjacent annular segments 212. In some embodiments, the connectors 220a may be relatively straight and may be elongated in the longitudinal direction. Moreover, in some embodiments, one or more of the connectors 220a that interconnect adjacent annular segments 212 may be configured with one or more marker eyelets 248a. In some embodiments there may be between 2 and 6 marker eyelets 248 around the circumference of the stent, including embodiments with about 4 total markers. A radiopaque tantalum (Ta) marker may be laser welded, swaged, or mechanically forced or fit bonded to one or more of these eyelets 248 in some embodiments. In other embodiments, any material which is visible via x-ray or fluoroscopic imaging may be used, for example, high density metals such as gold, platinum, tantalum, and so on. The marker may also or alternatively be riveted to the eyelets 248. A radiopaque marker may be utilized to position the stent 200 within the body of a patient. In some instances the marker eyelets 248 may be positioned at the same longitudinal location along the stent 200 as a proximal most edge of the valve 250.

As shown in FIG. 2A, in some embodiments, adjacent diamond-shaped cells need not be interconnected to one another by connectors 220. For example, apexes 215a, 215b of adjacent diamond-shaped cells are not connected to one another via a connector 220. A stent 200 designed such that each diamond-shaped cell is not interconnected to every adjacent diamond-shaped cell via a connector 220 may provide added flexibility to the stent 200. Additionally, areas in the stent 200 that are designed such that each diamond-shaped cell is not interconnected to every adjacent diamond-shaped cell via a connector 220 may be relatively softer as compared to areas of the stent 200 that are designed such that each diamond-shaped cell is interconnected to adjacent diamond-shaped cells via a connector 220.

Figure 3:
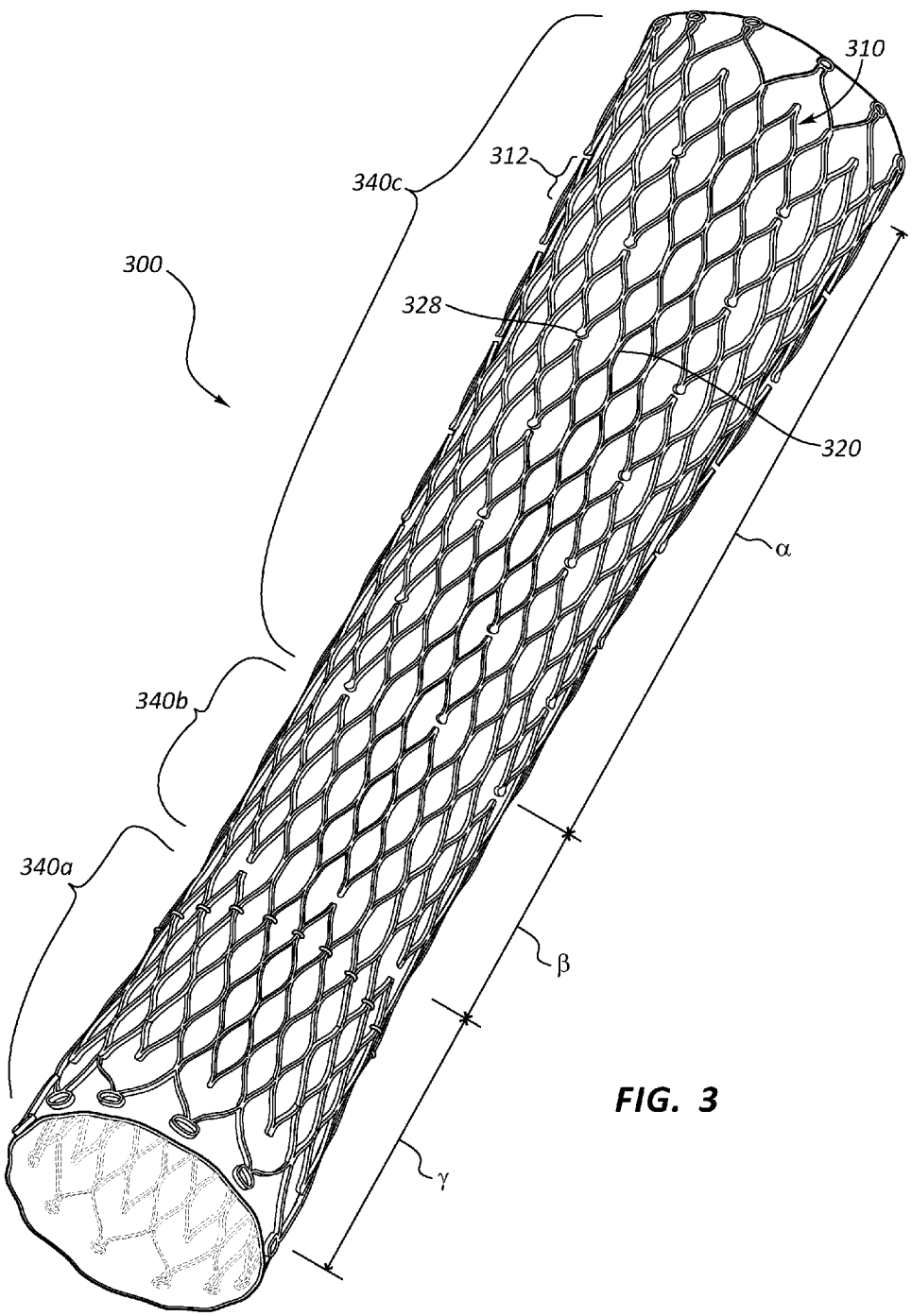
FIG. 3 is a perspective view of another embodiment of a stent.

FIG. 3 is a perspective view of another embodiment of a stent 300 having a plurality of adjacent annular segments 312 that are aligned and interconnected to form lattice structures 340a, 340b, 340c. The lattice structures 340a, 340b, 340c may form the valve zone γ, transition zone β, and proximal zone α. As shown in FIG. 3, in some embodiments, the stent 300 may comprise a plurality of lattice structures 340a, 340b, 340c disposed on a circumference and defining at least a portion of the generally cylindrical shape of the scaffolding structure 310. In the illustrated embodiment, the plurality of lattice structure 340a, 340b, 340c are arranged adjacent to one another in the longitudinal direction of the generally cylindrical shape of the scaffolding structure 310. In some embodiments, the lattice structures 340a, 340b, 340c comprise and/or define substantially diamond-shaped cells.

As previously discussed, in some embodiments, a plurality of connectors 320 may interconnect adjacent annular segments 312. The number of connectors 320 interconnecting adjacent annular segments 312 may be configured to affect the properties of the stent 300 in a particular zone on the stent 300. For example, the stent 300 may be configured such that there are a greater number of connectors 320 per annular segment 312 in the valve zone γ compared to the transition zone β, and a greater number of connectors 320 per annular segment 312 in the transition zone β compared to the proximal zone α. Accordingly, in the embodiment of FIG. 3, the lattice structures 340a, 340b, comprised of adjacent annular segments 312 in the valve zone γ and transition zone β, have a greater number of connectors 320 as compared to the lattice structure 340c comprised of adjacent annular segments 312 in the proximal zone α.

The stent 300 of the embodiment of FIG. 3 may comprise generally rounded anti-migration portions 328 coupled to certain diamond-shaped cells within the proximal zone α. As previously discussed, in some embodiments, the anti-migration portions 328 may be configured to contact portions of the inside diameter of a body lumen, and thus restrict migration of the stent 300 within the body lumen.

Figure 4:
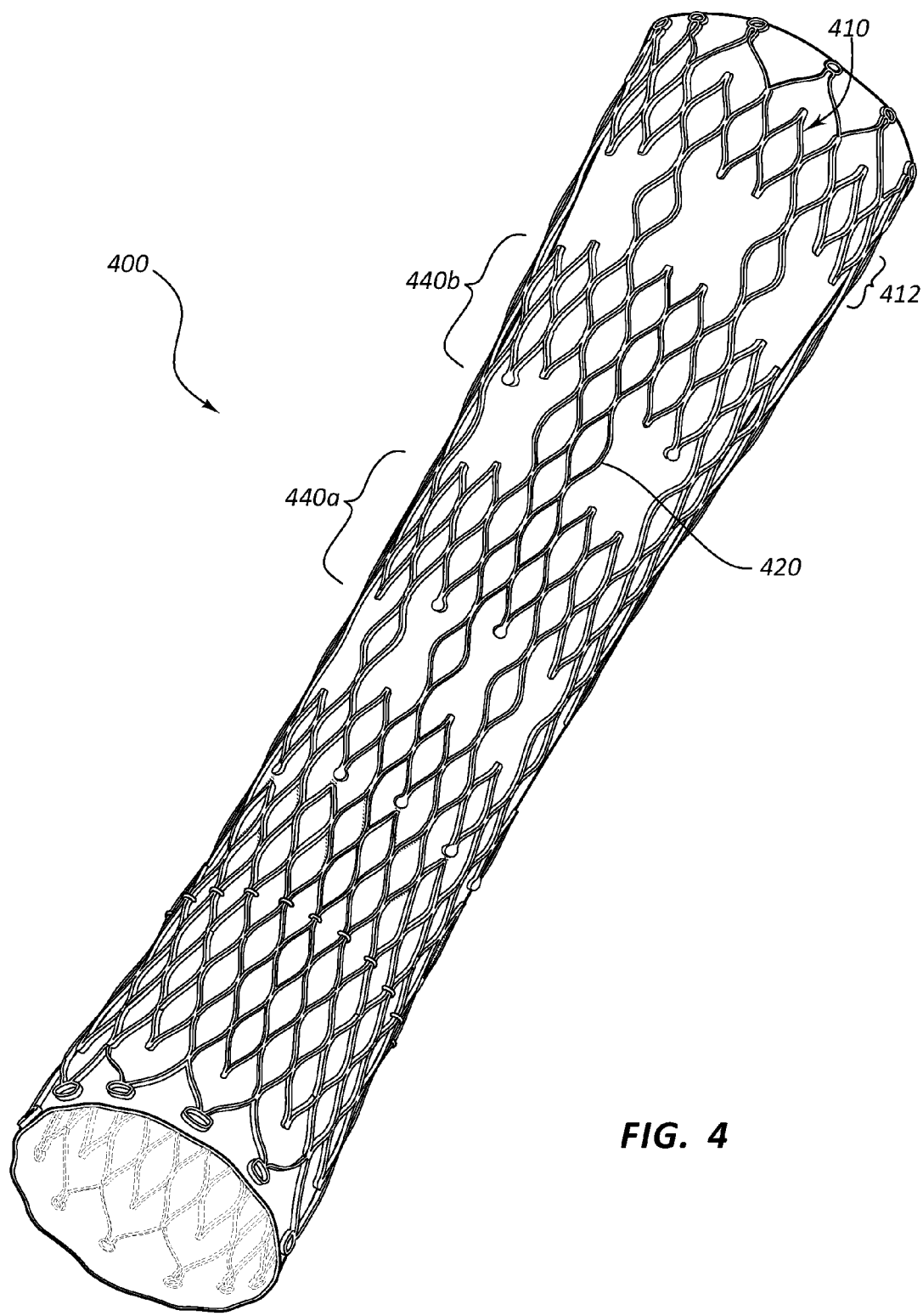
FIG. 4 is a perspective view of another embodiment of a stent.

FIG. 4 is a perspective view of another embodiment of a stent 400 having pluralities of adjacent annular segments 412 aligned and interconnected to form a plurality of lattice structures 440a, 440b. The plurality of lattice structures 440a, 440b may be disposed on a circumference and define at least a portion of the generally cylindrical shape of a scaffolding structure 410 of the stent 400. In the illustrated embodiment, the plurality of lattice structures 440a, 440b is arranged adjacent to one another in the longitudinal direction of the generally cylindrical shape. In some embodiments, the lattice structures comprise and/or define substantially diamond-shaped cells.

As illustrated in FIG. 4, adjacent lattice structures 440a and 440b may be interconnected by one or more connectors 420. In some embodiments, such as the embodiment of FIG. 4, the connectors 420 may be substantially diamond-shaped. In some embodiments, each diamond-shaped cell in a lattice structure 440a is not interconnected to each diamond-shaped cell in an adjacent lattice structure 440b via a diamond-shaped connector 420. Interconnecting adjacent lattice structures 440a, 440b in the stent 400 in this fashion may provide the stent 400 with certain desired characteristics. For example, portions of the stent 400 comprising less connectors 420 may be relatively softer than portions of the stent 400 comprising more connectors 420.

FIGS. 5A-5D are partially cut-away views of additional embodiments of a stent 500 according the present disclosure. As shown in FIGS. 5A-5D, the scaffolding structure 510 may comprise one or more rows of strut arms 514 arranged and interconnected in a series of turns 542 to form a helix or helical pattern 544 that wraps or winds around the longitudinal axis $A_L$ of the stent 500. The helical pattern 544 of strut arms 514 may be disposed on a circumference and may define at least a portion of the generally cylindrical shape of the scaffolding structure 510. As can be appreciated, in some embodiments, the entire length of the stent 500 may comprise a helical pattern 544 of interconnected strut arms 514. In other embodiments, however, only a portion of the stent 500, for example, the proximal zone α, transition zone β, or valve zone γ (shown in FIG. 1), may comprise a helical pattern 544. The helical pattern 544 may be right-handed or left-handed depending on which direction the one or more rows of strut arms 514 wrap around the longitudinal axis $A_L$.

Figure 5A:
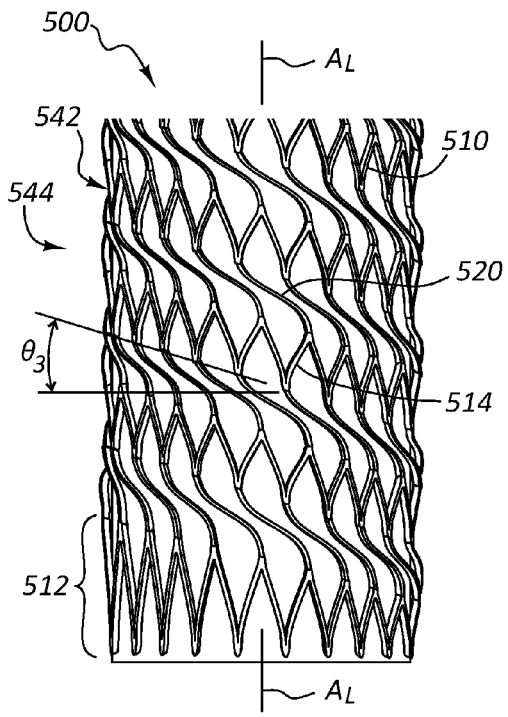
FIGS. 5A-5D are partially cut-away views of additional embodiments of a stent.
Figure 5B:
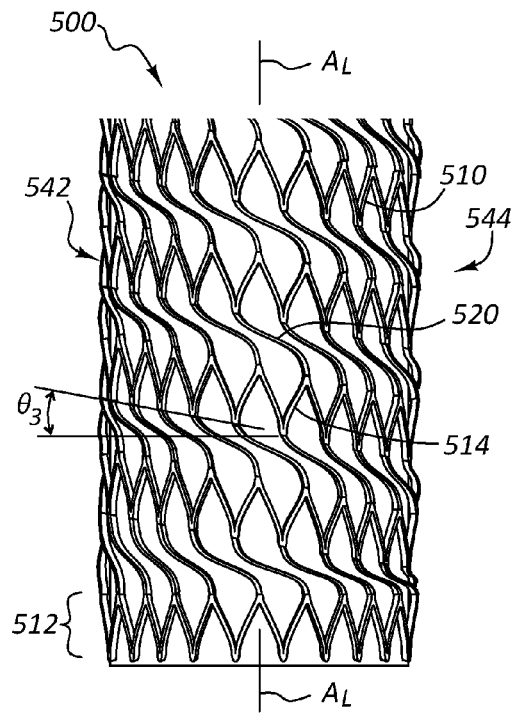

As further illustrated in FIGS. 5A and 5B, the helical pattern 544 may comprise a row of strut arms 514 arranged to form a zigzag pattern, defining alternating "peaks" and "valleys," that may wrap around the longitudinal axis $A_L$ of the stent 500. In some embodiments, the "peaks" and "valleys" on a row of strut arms 514 may be coupled by connectors 520. In particular, the "peaks" on one turn 542 of the helical pattern may be coupled to the "valleys" on an adjacent turn 542 of the helical pattern 544 via connectors 520. As used herein, a "turn" of the helical pattern refers to a segment of strut arms 514 that wraps 360 degrees around the longitudinal axis $A_L$ of the stent 500. Adjacent turns 542 of the helical pattern 544 may adjoin each other at an end.

As illustrated in FIGS. 5A and 5B, the helical pattern 544 may wrap around the longitudinal axis $A_L$ of the stent 500 at an angle $\theta_3$. The degree of the angle $\theta_3$ may vary and may affect the structural properties of the stent 500. In some embodiments, the angle $\theta_3$ may remain substantially constant throughout the helical pattern 544. In other embodiments, however, the angle $\theta_3$ may vary throughout the helical pattern 544.

In some embodiments, one or more annular segments 512 comprising strut arms 514 may be disposed adjacent to the distal and/or proximal ends of the helical pattern 544, as is shown in FIGS. 5A and 5B. The one or more annular segments 512 may be coupled to, for example a first turn 542 of strut arms 514 of the helical pattern 544 in a variety of ways. As illustrated in FIG. 5A, an annular segment 512 may be coupled to the helical pattern 544 by connectors 520. In some embodiments, each connector 520 used to couple an annular segment 512 to a first turn 542 of the helical pattern 544 may be substantially the same length. The angle $\theta_3$ of the helical pattern 544 may therefore be achieved by gradually increasing the length of the strut arms 514 on the annular segment 512. Accordingly, a greater increase in the length of the strut arms 514 on the annular segment 512 yields an angle $\theta_3$ with a higher degree.

As illustrated in FIG. 5B, in some embodiments, the annular segment 512 coupled to the first turn 542 of the helical pattern 544 may comprise strut arms 514 that are substantially the same length. The angle $\theta_3$ of the helical pattern may therefore be achieved by gradually increasing the length of the connectors 520 used to couple the annular segment 512 to the first turn 542 of the helical pattern 544. Accordingly, a greater increase in the length of connectors 520 yields an angle $\theta_3$ with a higher degree.

Figure 5C:
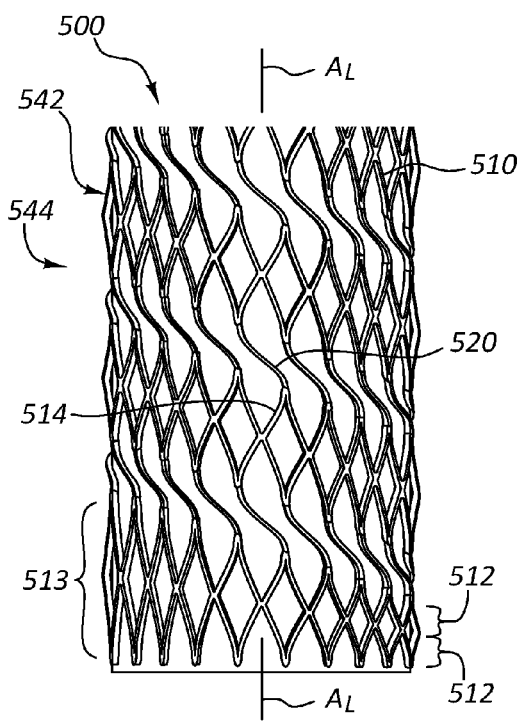
Figure 5D:
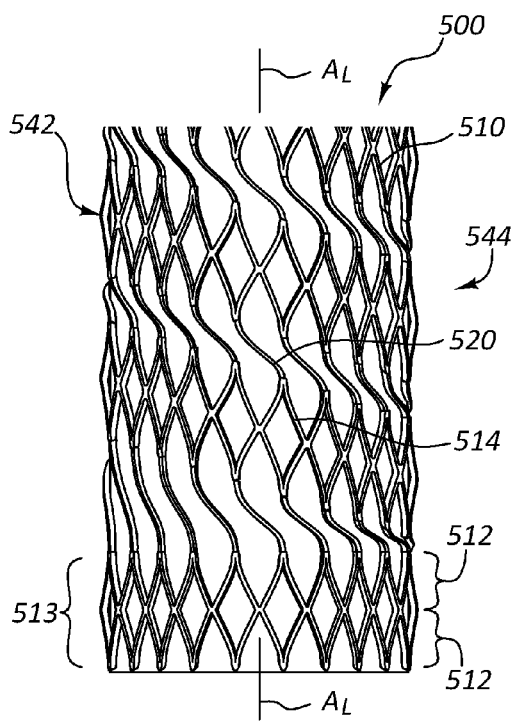

In the embodiments of FIGS. 5C and 5D, two adjacent parallel rows of strut arms 514 may be coupled such that they form diamond-shaped cells along the helical pattern 544. Accordingly, in some embodiments, the helical pattern 544 may comprise substantially diamond-shaped cells. In some embodiments, the diamond-shaped cells may comprise strut arms 514 that are substantially equal in length. In other embodiments, the diamond-shaped cells may comprise strut arms 514 of varying lengths.

As is shown in FIGS. 5C and 5D, in some embodiments, a row of substantially diamond-shaped cells 513 comprising two annular segments 512 of strut arms 514 may be disposed adjacent to the distal and/or proximal ends of the helical pattern 544. The one or more annular segments 512 may be coupled to the helical pattern 544 in a variety of ways. As illustrated in FIG. 5C, the row of diamond-shaped cells 513 may be coupled to the helical pattern 544 by connectors 520. In some embodiments, each connector 520 used to couple the row of diamond-shaped cells 513 to the helical pattern 544 may be substantially the same length. The angle $\theta_3$ of the helical pattern may therefore be achieved by gradually increasing the length of strut arms 514 within the row of diamond-shaped cells 513.

As illustrated in FIG. 5B, in some embodiments, the row of diamond-shaped cells 513 coupled to the helical pattern 544 may comprise strut arms 514 that are substantially the same length. The angle $\theta_3$ of the helical pattern 544 may therefore be achieved by gradually increasing the length of the connectors 520 used to couple the row of diamond-shaped cells 513 to the first turn 542 of the helical pattern 544.

Figure 6A:
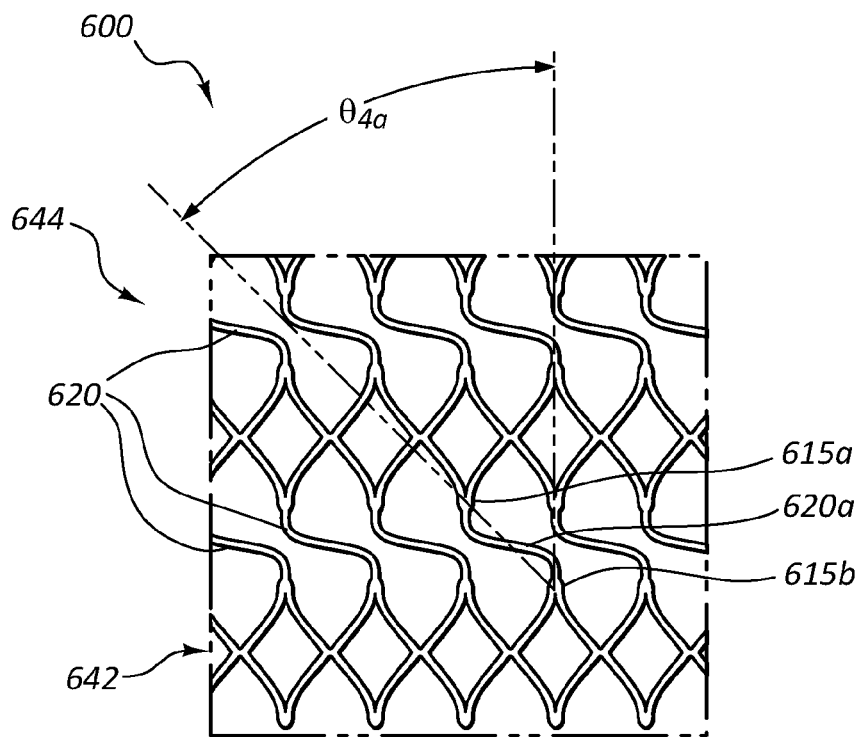
FIGS. 6A and 6B are close-up views of portions of a stent, according to an embodiment of the present disclosure.
Figure 6B:
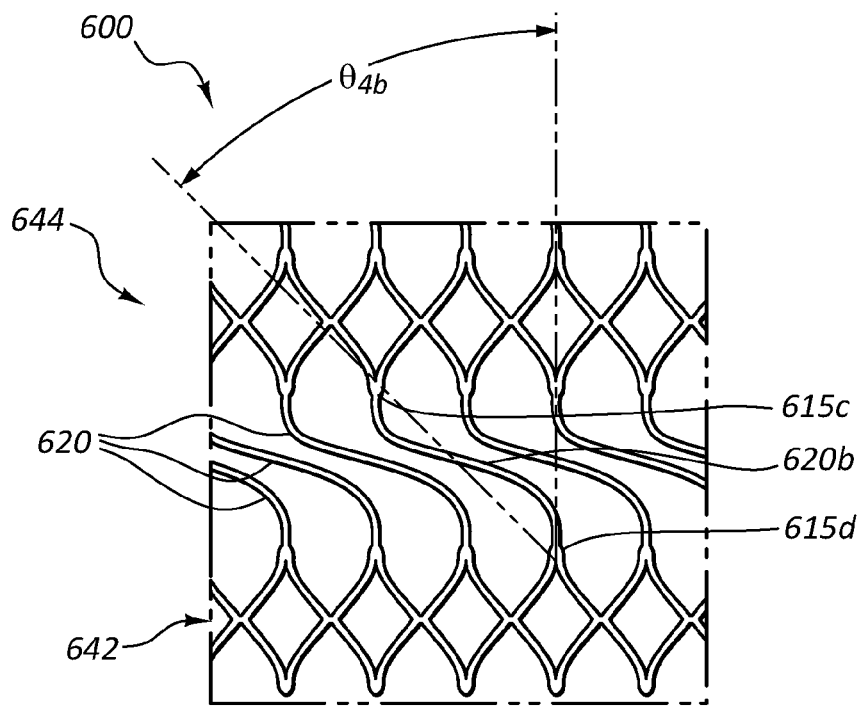

FIGS. 6A and 6B are close-up views of a portion of a stent 600 according to an embodiment of the present disclosure. As shown in FIGS. 6A and 6B, the connectors 620 may couple adjacent turns 642 of the helical pattern 644 in a variety of ways. For example, in the illustrated embodiment of FIG. 6A, a connector 620a is coupled to the apex 615a and the apex 615b. The coupled apexes 615a, 615b are not aligned along the longitudinal direction of the stent 600. Rather, the coupled apexes 615a, 615b are offset from the longitudinal axis by an angle $\theta_{4a}$. Similarly, in the illustrated embodiment of FIG. 6B, a connector 620b is coupled to an apex 615c and an apex 615d. The coupled apexes 615c, 615d are not aligned along the longitudinal direction of the stent 600 and instead are offset by an angle $\theta_{4b}$. In some embodiments, the angle $\theta_4$ may be about 45 degrees or less to maintain sufficient hoop forces along the stent 600.

Figure 7A:
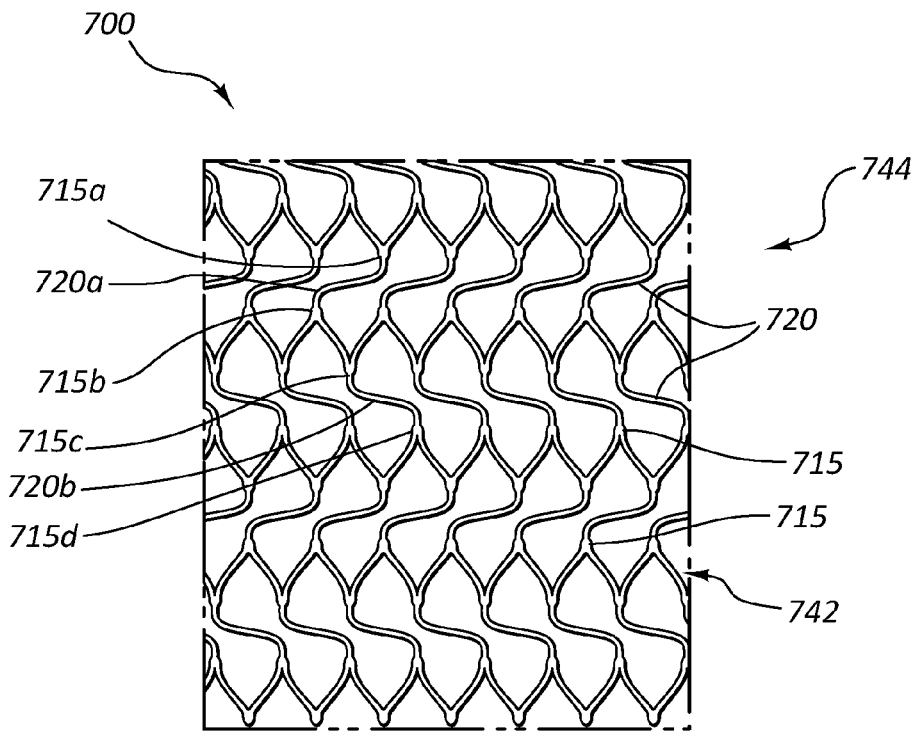
FIGS. 7A and 7B are close-up views of portions of a stent, according to an embodiment of the present disclosure.
Figure 7B:
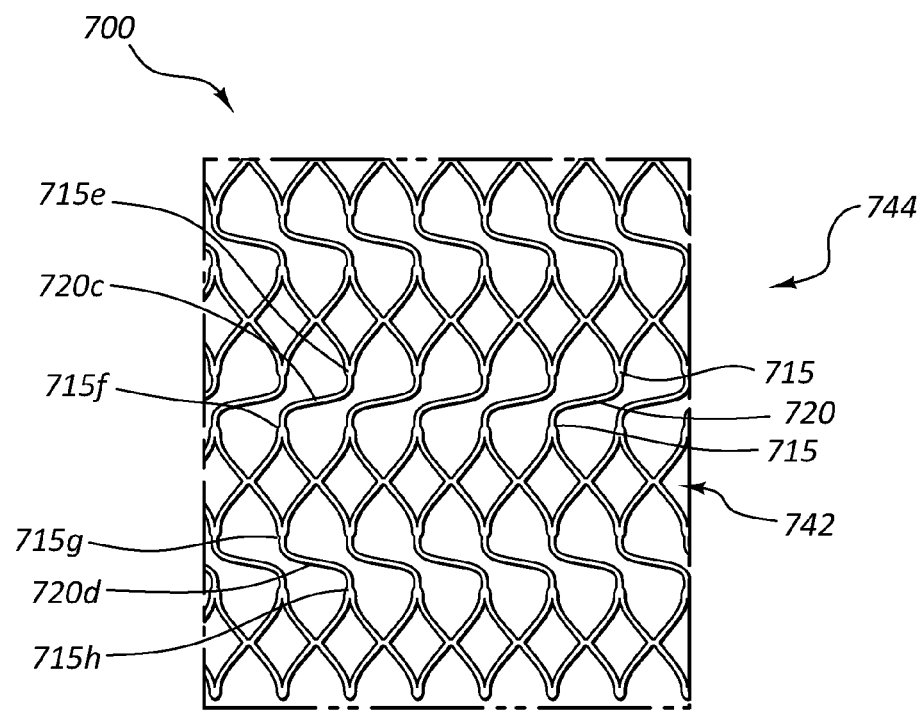

FIGS. 7A and 7B are close-up views of embodiments of a stent 700 according to the present disclosure. As shown in FIGS. 7A and 7B, the orientation and manner in which the connectors 720 couple adjacent turns 742 of a helical pattern 744 may vary. For example, as shown in FIG. 7A, a connector 720a couples an apex 715b to an apex 715a that is offset to the right. On the other hand, a connector 720b couples an apex 715d to an apex 715c that is offset to the left. Similarly, as shown in FIG. 7B, a connector 720c couples an apex 715f to an apex 715e that is offset to the right, while a connector 720d couples an apex 715h to an apex 715g that is offset to the left. Moreover, in some embodiments, there may be two or more consecutive turns 742 of the helical pattern 744 coupled by connectors 720 wherein the coupled apexes 715 are each offset in one direction followed by two or more consecutive turns 742 of the helical pattern 744 coupled by connectors 720 wherein the coupled apexes 715 are each offset in an opposite direction.

Figure 8A:
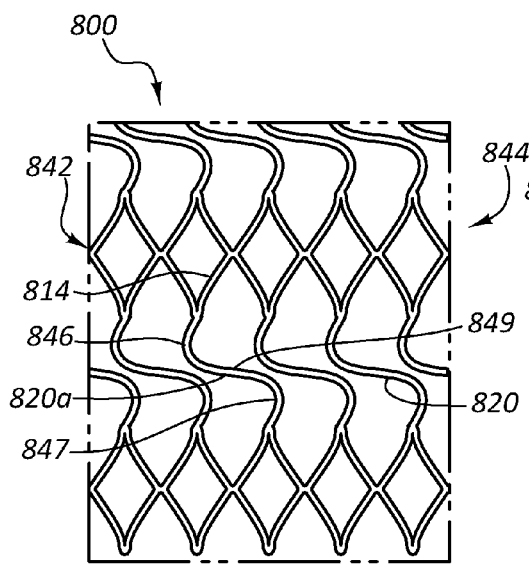
FIGS. 8A-8D are close-up views of portions of a stent, according to an embodiment of the present disclosure.
Figure 8B:
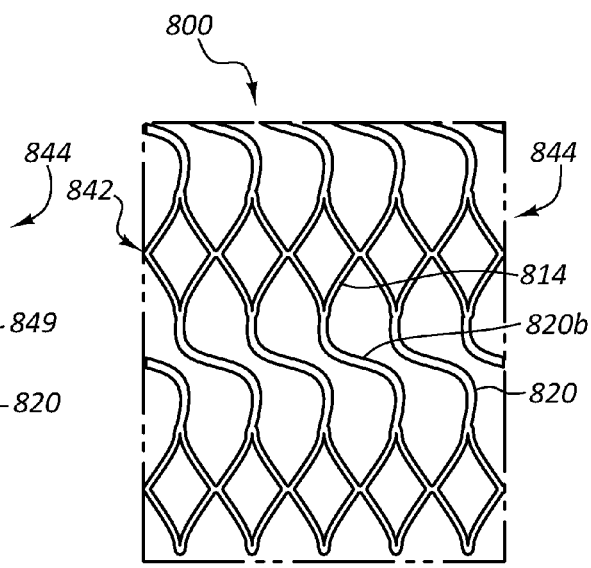

FIGS. 8A-8D are close-up views of various connectors 820 that may be used to interconnect one or more rows or turns 842 of strut arms 814 arranged in a helical pattern 844. For example, as illustrated in FIG. 8A, a connector 820a may be sigmoid shaped, or "S" shaped. In other words, a first portion 846 of the connector 820a forms a first roughly arcuate path, and a second portion 847 of the connector 820a forms a second roughly arcuate path. A center of the first arcuate path may be on the opposite side of the connector 820a from a center of the second arcuate path. Thus, the connector 820a may have a wave-like shape formed by the connector 820a starting to curve in one direction, and then curving in a second direction. Accordingly, the connector 820a may have an "inflection point" 849 at or around the mid-point of the connector 820a. Additionally, a sigmoid or "S" shaped connector may be designed to have more or less curvature. For example, as shown in the embodiment of FIG. 8B, a connector 820b may have less curvature than the connector 820a of FIG. 8A. In other embodiments, however, the connectors 820 may have more curvature.

Figure 8C:
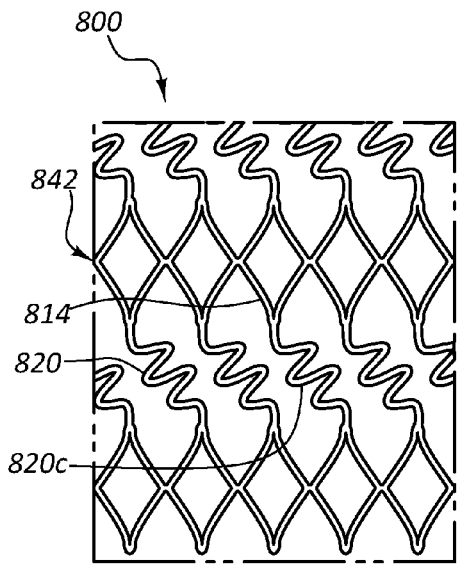
Figure 8D:
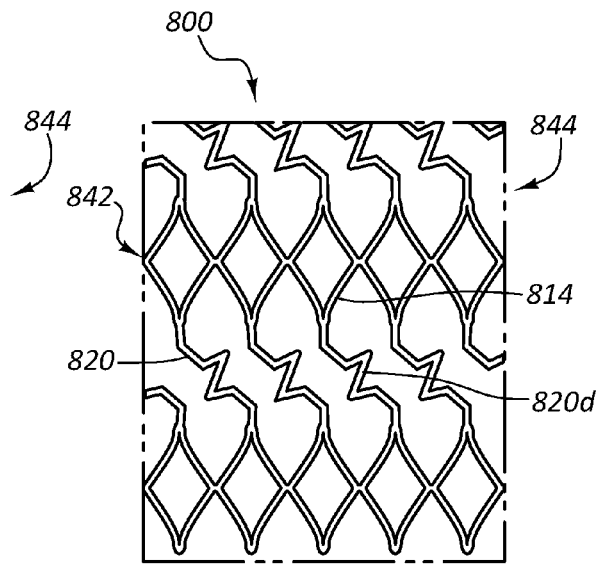

Additional shapes of connectors 820 are within the scope of the present disclosure. For example, as shown in the embodiment of FIG. 8C, a connector 820c may include one or more sinusoidal shaped waves. As shown in the embodiment of FIG. 8D, a connector 820d may include one or more teeth or "V" shaped segments. As can be appreciated, the connectors 820 depicted in FIGS. 8A-8D are designed such that adjacent connectors 820 may nest together when the stent 800 is in an unexpanded state. Accordingly, any shape and/or size of connector 820 that is capable of nesting with adjacent connectors 820 is within the scope of the present disclosure.

FIG. 9 is a front view of another embodiment of a stent 900. The stent 900 defines a proximal end 902 and a distal end 904 as well as a mid-body section 903. The stent 900 may have a smaller diameter near the mid-body section 903 than sections of the stent 900 near the proximal 902 and distal ends 904. Thus, in the illustrated embodiment, $D_2$ and $D_3$ may be larger in magnitude than $D_1$. In some embodiments, the mid-body diameter may be constant along a length of the stent 900, with flare portions that gradually increase in diameter near the ends 902 and 904. Depending on the desired application, the diameters of the stent 900 may vary. For example, certain stents may be designed with mid-body diameters of about 12 mm to about 25 mm, including stents with diameters from about 19 mm to about 23 mm. In embodiments which include flared zones near the ends of the stent 900, the diameter of the flared sections may increase from about 2 mm greater to about 8 mm greater than the mid-body diameter of the stent, including increases of about 4 mm to about 6 mm or an increase of about 5 mm or increase of about 2 mm to about 4 mm, including increases of about 3 mm. While in some embodiments the stent 900 may increase by about the same magnitude at both the proximal 902 and distal 904 ends, in other embodiments, such as the embodiment of FIG. 9, the increases may be different. For example, in the embodiment of FIG. 9, $D_2$, or the diameter at the proximal end, may be about 5 mm greater than $D_1$, the mid-body diameter of the stent 900, while $D_3$ may be about 3 mm greater than $D_1$.

In embodiments where the strut arms 914 are relatively longer (creating relatively "softer" zones near the ends 902, 904 of the stent 900) the flare section may correlate with the zones of the stent 900 that have relatively longer strut arms 914. The strut arm 914 length may be configured to gradually increase along the longitudinal direction of the stent 900 in the flare zones.

Similarly, the length of the connectors 920 may gradually increase as the strut arm 914 length increases. Longer connectors 920 and arm struts 914 may generally create a more open scaffolding structure 910 near the ends 902, 904 of the stent 900. In some embodiments, the flare zones may be mirror images of each other; in other embodiments they may be different.

In some embodiments, the flare zones may be formed by stretching or expanding the ends 902, 904 of the stent 900 with respect to the mid-body 903 of the stent 900. This may result in a more open scaffolding structure 910 near the ends of the stent 900. Regions of the stent 900 with a more open scaffolding structure 910 may be relatively softer than regions of the stent 900 which have a denser scaffolding structure 910. Thus, the flared ends of the stent 900, may be configured to create ends that are softer than the mid-body 903 of the stent 900. As disclosed above, relatively longer strut arms 914 and connectors 920 may also be configured to create softer regions of the stent 900. Flared ends and changing strut arm lengths and connector lengths may each be designed and/or may utilize independently from, or in connection with, these other parameters in order to create a stent 900 with relatively softer, or stiffer, zones.

The stent 900 may be configured to neck down in a similar manner to that described in connection with the stent 100 of FIG. 1. In some embodiments, the flared portions of the stent 900 may be configured to neck down to a diameter less than the diameter of a mid-body section of the stent. In certain embodiments, a mid-body section may not be configured to neck down.

FIGS. 9A-9B are additional views of the stent 900 of FIG. 9. FIG. 9A is a top view of the stent of FIG. 9, viewing the stent 900 from the proximal end 902, and FIG. 9B is a cross-sectional view of the stent of FIG. 9, taken through line 9B-9B. FIGS. 9A and 9B both illustrate a valve 950 coupled to the inside diameter of the stent 900. As shown in FIG. 9, the valve 950 may be located within the valve zone γ of a stent 900, and may be positioned closer to the distal end 904 of the stent 900 than to the proximal end 902.

The valve 950 may be coupled to the stent 900 by one or more rows of stitching 954 around the circumference of the stent 900. In other embodiments the valve 950 may alternatively or additionally be coupled to the stent 900 through use of an adhesive, a plurality of ties, through welding, through caulking, and through other attachment methods. For example, in some embodiments the valve 950 may be positioned within the stent 900 prior to applying a coating to the stent 900. Application of the coating may serve to simultaneously bond the valve to the coating in some instances.

FIGS. 9 and 9A also illustrate suture threading eyelets 936 and a suture 935 configured for use in connection with the stent 900. The suture 935 may be configured to allow a practitioner to engage the suture 935 in order to aid in removing and/or repositioning the stent 900. In some instances this may be accomplished by the practitioner grasping and displacing the suture 935 through use of a remote access tool, such as grasping forceps. The suture 935 may be formed of a metal, a thread, or any other material. In some embodiments, the suture 935 may comprise one or more radiopaque portions 938 for use in deploying, removing, or repositioning a stent. The radiopaque portions may be formed of a metal, such as gold, and enable a practitioner to distinguish these portions by x-ray, fluoroscopy, or similar methods, thus allowing the practitioner to more easily capture the suture 935 of a deployed stent with a remote capturing tool. Similarly, the suture 935 may also or alternatively comprise endoscopic markers, or markers visible through an endoscope, to aid a practitioner in viewing or manipulating the stent in connection with an endoscope. In some embodiments certain markers, such as markers comprised of gold, may be both radiopaque and visible through an endoscope.

Figure 10:
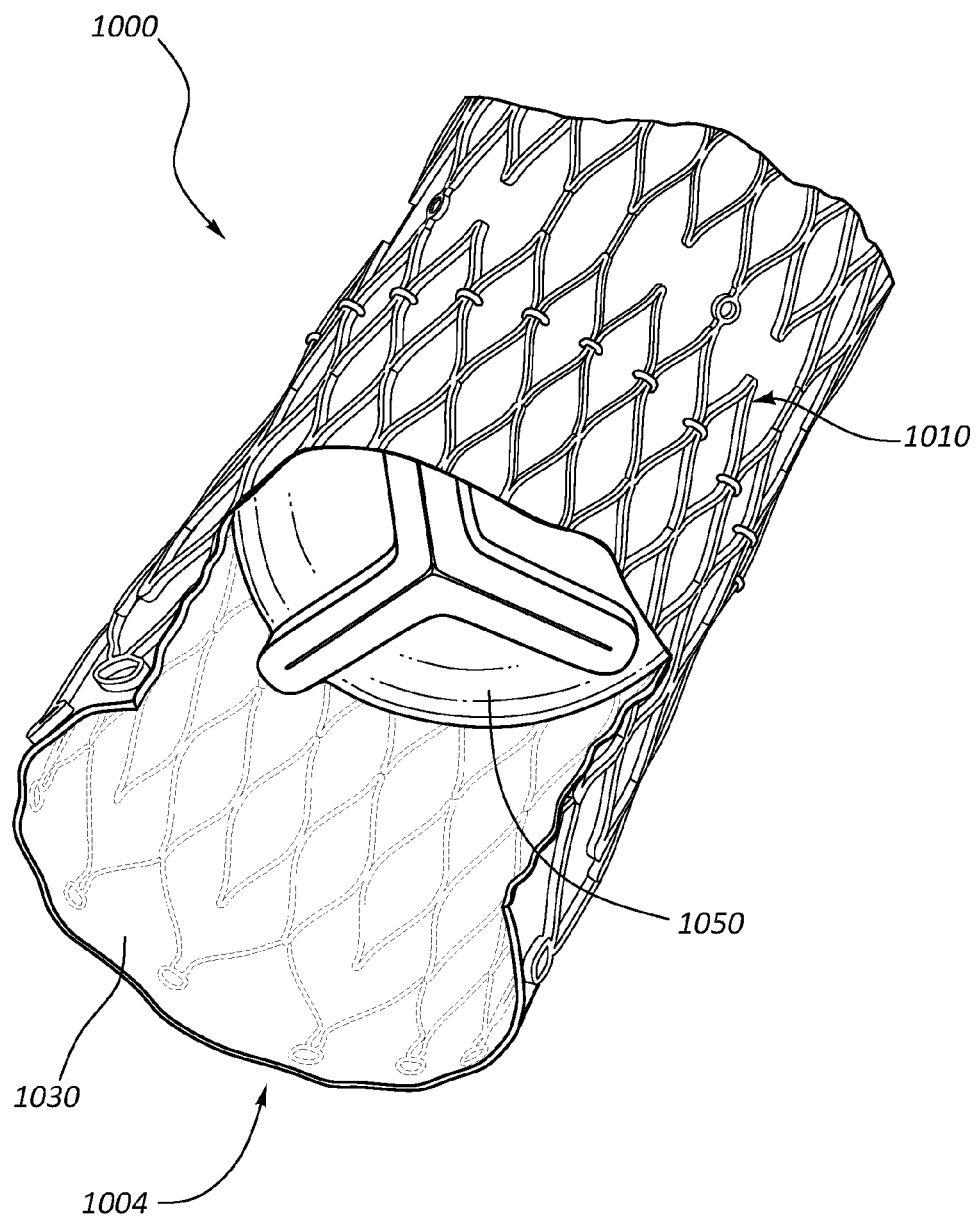
FIG. 10 is a partially cut-away perspective view of another embodiment of a stent.

FIG. 10 is a partially cut-away perspective view of a portion of a stent 1000 including a valve 1050. The stent 1000 has a distal end 1004, a cover 1030, and a scaffolding structure 1010. The stent 1000 is oriented such that the valve 1050 is visible through the opening at the distal end 1004 of the stent 1000. In other embodiments, the valve 1050 may be positioned at other locations along the longitudinal length of the stent 1000, including locations closer to the proximal end (not shown) or distal end 1004 of the stent 1000. For example, the valve 1050 may be positioned at the very last distal row such that a portion of the valve may hang outside of the scaffolding structure of the stent 1000. Accordingly, the valve 1050 may be positioned at any point and in any portion of the stent 600.

FIGS. 11A-11D are multiple views of a valve 1150 configured for use with a stent. The valve 1150 may be formed of an elastomeric or polymeric material and may comprise an upper surface 1151, a lower surface 1152, and a rim 1153. The rim 1153 may provide structure and support to the valve 1150 as well as providing a location at which the valve 1150 may be coupled to a stent, for example, by stitching.

Figure 11A:
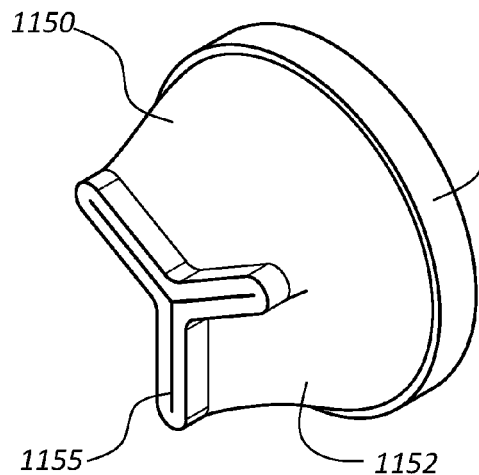
FIG. 11A is a perspective view of a valve for use with a stent, according to one embodiment.
Figure 11B:
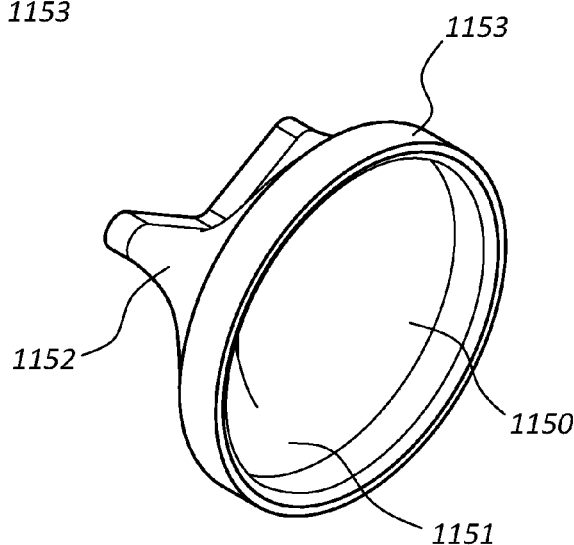
FIG. 11B is a second perspective view of the valve of FIG. 11A.
Figure 11C:
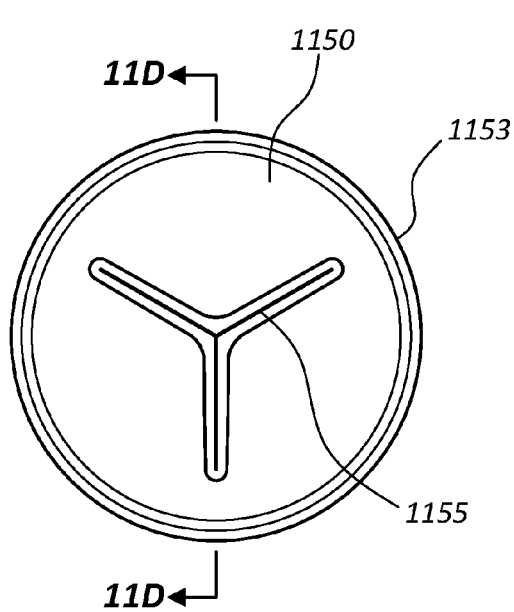
FIG. 11C is a top view of the valve of FIG. 11A.
Figure 11D:
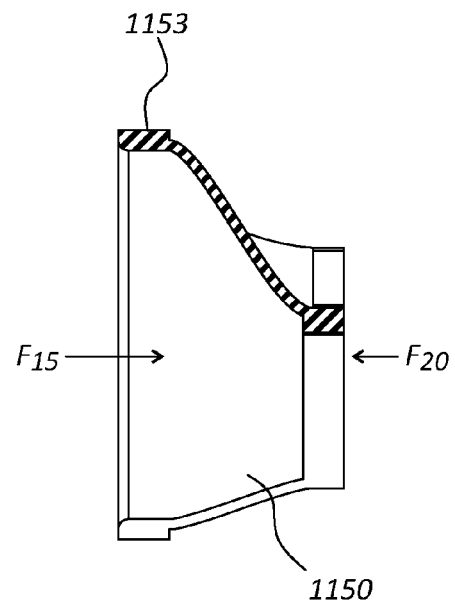
FIG. 11D is a cross-sectional view of the valve of FIG. 11C, taken through line 11D-11D.

The valve 1150 may further comprise an opening 1155 which is closed when the valve 1150 is not actuated. In the illustrated embodiment, the valve opening 1155 comprises three intersecting slits in the valve body. The valve opening 1155 may be opened in response to a force acting on the upper surface 1151 of the valve 1150. Likewise, the valve may be opened by a force acting on the lower surface 1152 of the valve 1150. The shape and design of the valve 1150 may be such that the force required to open the valve 1150 by acting on the lower surface 1152 is much larger than the force required to open the valve 1150 by acting on the upper surface 1151. For example, FIG. 11D illustrates two forces, $F_{15}$ acting on the upper surface 1151 of the valve 1150 and $F_{20}$ acting on the lower surface 1152 of the valve 1150. In response to $F_{15}$, the three-sided valve opening 1155 may relatively easily open, as opposing sides of the opening 1155 are pushed away from each other. Contrarily, in order for $F_{20}$ to open the valve 1150, the entire lower surface 1152 must deform, folding in on itself until the valve opening 1155 is located on the opposite side of the rim 1153. Thus, the valve 1150 may be designed such that it is more easily opened in one direction than the other.

In the case of esophageal stents, a valve such as valve 1150 may be positioned such that the lower surface 1152 faces the stomach while the upper surface 1151 faces the mouth. In this orientation, the valve 1150 may more readily open to allow food to pass to the stomach, but generally will prevent reflux from the stomach, except in response to a relatively large force—for instance when a patient belches or vomits.

Notwithstanding the specific disclosure provided in connection with FIGS. 11A-11D, it is within the scope of the current disclosure to utilize a stent with any type or design of valve, or without a valve at all.

Figure 12:
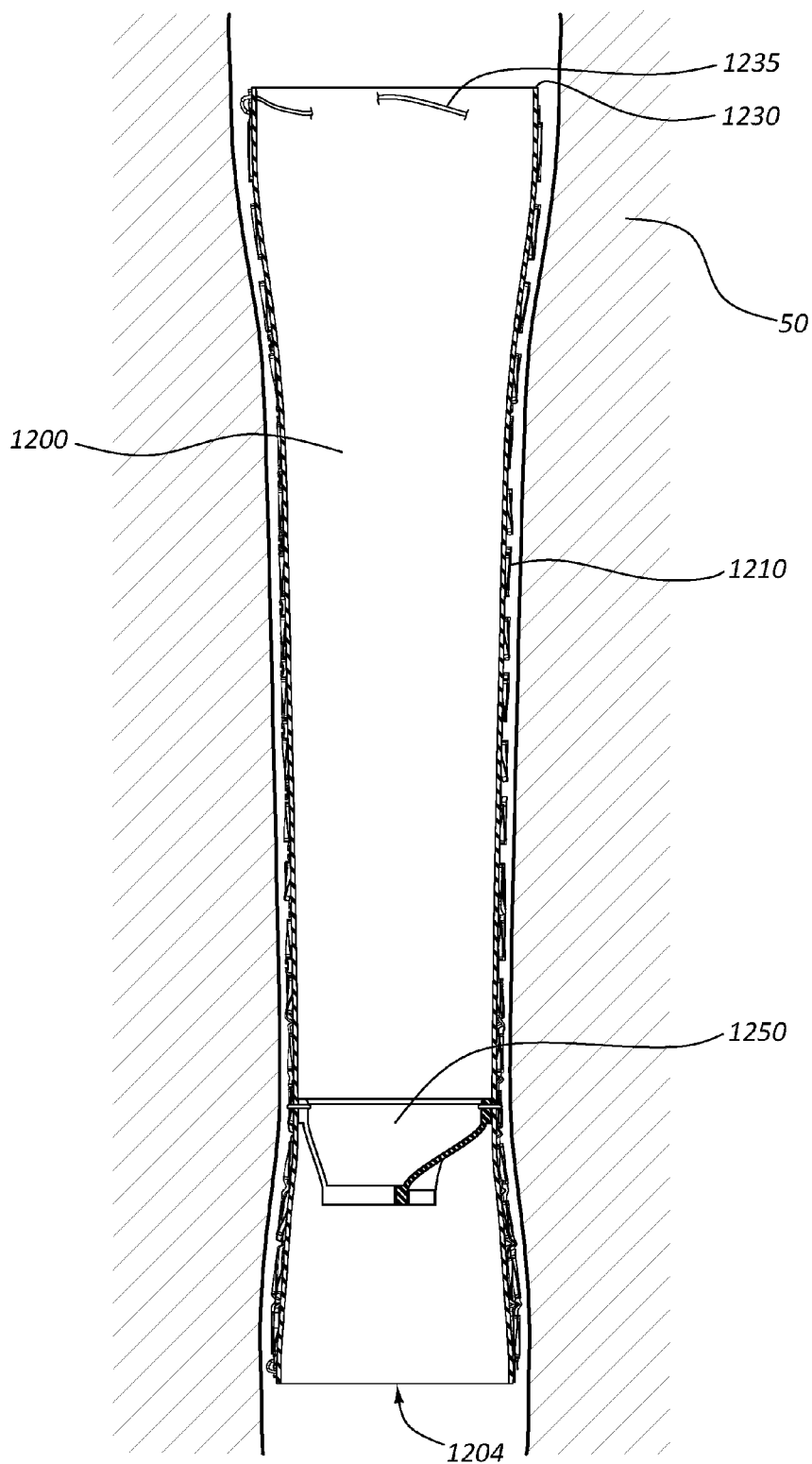
FIG. 12 is a cross-sectional view of a stent, according to one embodiment of the present disclosure, disposed within a body lumen.

FIG. 12 is a cross-sectional view of a stent 1200 deployed within a body lumen 50. The stent comprises a scaffolding structure 1210, a cover 1230, a suture 1235, and a valve 1250.

In some instances the body lumen 50 may be the esophagus. In these instances, a variety of stent placements are possible, including placements where a portion of the stent 1200 at the distal end 1204 extends into the stomach. In some instances, for example, the valve 1250 may be aligned with the lower esophageal sphincter and the distal end 1204 of the stent 1200 positioned within the stomach. In other embodiments, the valve 1250 may be aligned with the lower esophageal sphincter with the distal end 1204 of the stent 1200 located proximal to the stomach or flush with the stomach.

Figure 13:
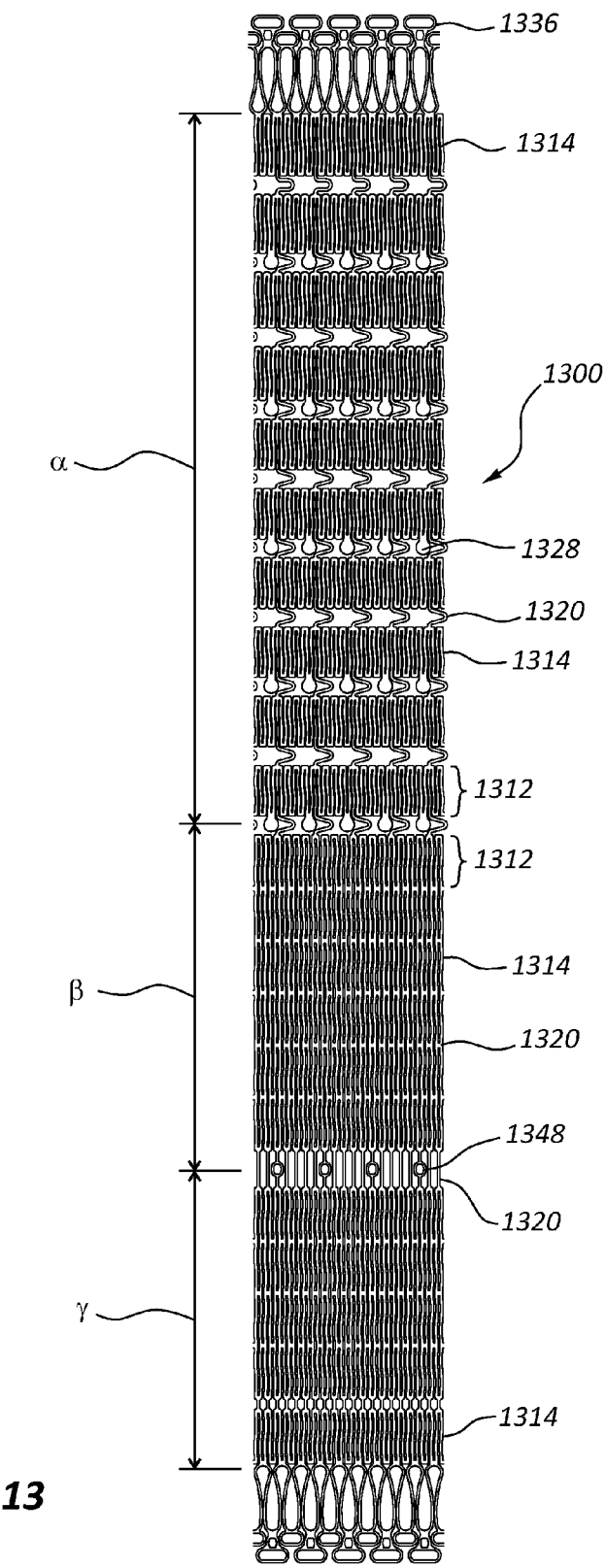
FIG. 13 is a side view of a stent, according to one embodiment of the present disclosure, in an unexpanded state. More particularly.

FIG. 13 is a side view of an embodiment of a stent 1300 in an unexpanded state. More particularly, FIG. 13 is a side view of an unexpanded stent in a "rolled out" state, depicted as if the stent 1300 was cut in the longitudinal direction and rolled out flat such that the entire circumference of the stent 1300 may be viewed flat.

In some embodiments, stent 1300 may be formed by cutting a pattern, such as that shown in FIG. 13, into a tube of material. In some embodiments, the tube of material from which the stent 1300 is cut may have a diameter from about 3 mm and about 8 mm, including from about 4 mm and about 6 mm, or about 5 mm. In some instances the tube of material may be a memory alloy, and the cutting may be accomplished through use of a laser. The cut tube may then be stretched and expanded. The unexpanded stent of FIG. 13 have many similar features to the other stents discussed herein, though the other stents were depicted in expanded states.

For example, the stent 1300 includes strut arms 1314 arranged to form annular segments 1312. The illustrated embodiment of FIG. 13B comprises 21 total rows of annular segments 1312. The stent 1300 further comprises valve γ, transition β, and proximal α zones. Adjacent annular segments 1312 disposed in the valve γ and transition β zones are aligned and interconnected such that they form diamond-shaped cells.

FIG. 13 further shows the relative positions of the strut arms 1314, suture threading eyelets 1336, marker eyelets 1348, connectors 1320, and anti-migration portions 1328 when the stent 1300 is in an unexpanded state.

Figure 14:
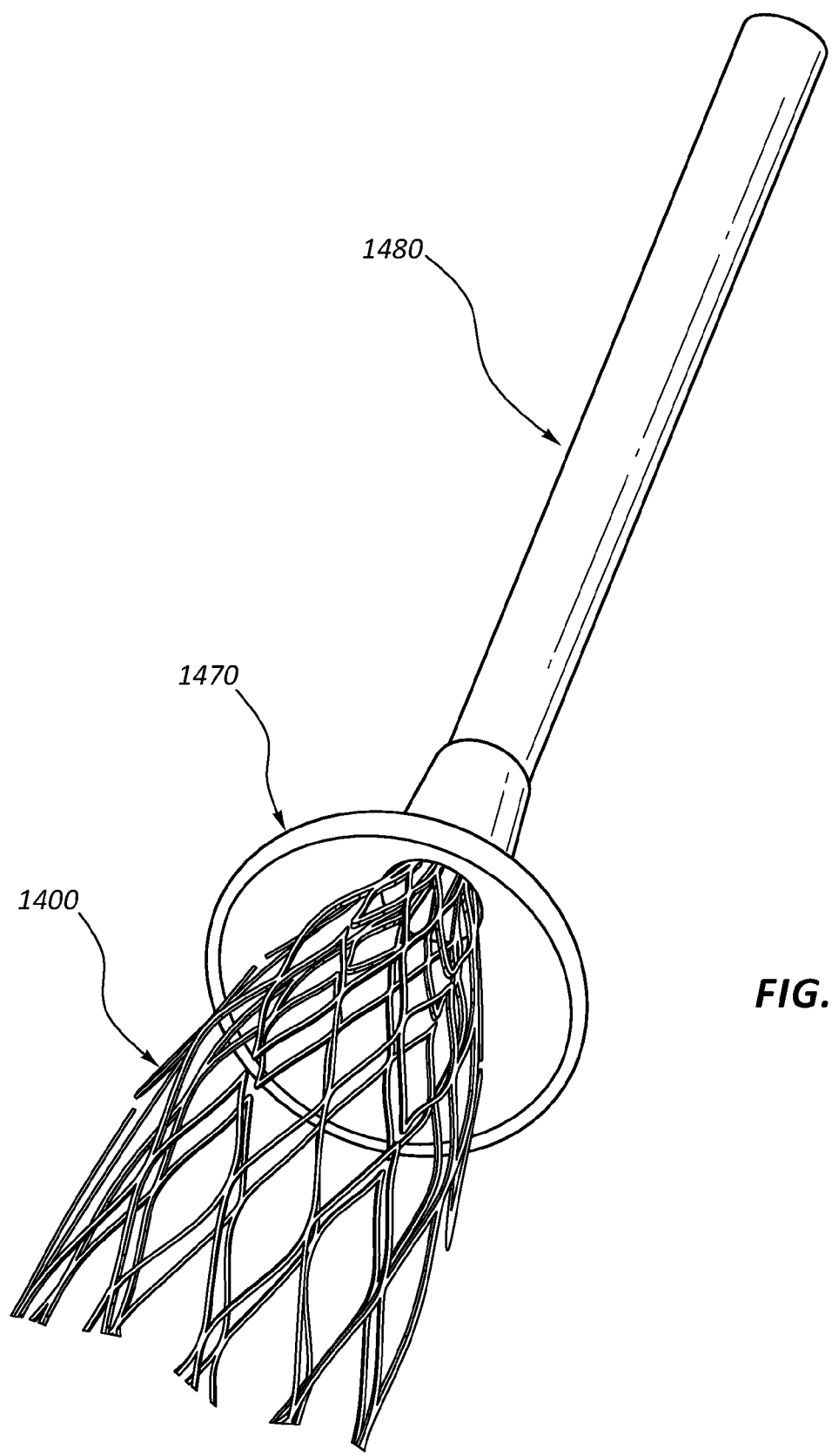
FIG. 14 is a perspective view of a stent according to one embodiment of the present disclosure, being fed through a funnel into a deployment sheath/catheter.

FIG. 14 is a perspective view of a stent 1400 being fed through a funnel 1470 into deployment sheath or catheter 1480. In the illustrated embodiment, the stent 1400 is arranged such that adjacent annular segments are interconnected to form diamond-shaped cells. As described above, in some embodiments, interconnecting adjacent annular segments to form diamond-shaped cells may aid in self loading of the stent 1400.

Numerous sizes and configurations of stents are within the scope of this disclosure. By way of example, and not limitation, in addition to esophageal stents, the current disclosure is also applicable to biliary stents and other stents which may utilize a valve. In some embodiments this disclosure may be used with such stents in the following sizes and dimensions. Biliary stents: mid-body diameters from about 6 mm to about 11 mm including diameters of about 8 mm to about 10 mm; flare sections configured to expand from about 0.5 mm to about 2 mm in diameter greater than the mid-body diameter of the stent; and lengths of from about 40 mm to about 100 mm, including lengths from about 60 mm to about 80 mm.

Additional embodiments of a stent that may be used in accordance with the present disclosure are set forth in U.S. patent application Ser. No. 13/285,358, which is incorporated herein by reference.

The examples and embodiments disclosed herein are to be construed as merely illustrative and exemplary, and not a limitation of the scope of the present disclosure in any way. It will be apparent to those having skill with the aid of the present disclosure in the art that changes may be made to the details of the above-described embodiments without departing from the underlying principles of the disclosure herein. It is intended that the scope of the invention be defined by the claims appended hereto and their equivalents.

The invention claimed is:

1. An implantable device to be disposed within a body lumen, the implantable device comprising:
a scaffolding structure defining a cylindrical shape and a lumen through the scaffolding structure, wherein at least a first portion of the scaffolding structure comprises a lattice structure formed by a plurality of interconnected arms the first portion having a first stiffness, and a second portion of the scaffolding structure comprises a second plurality of interconnected arms with adjacent arms arranged at acute angles relative to each other in rows around a longitudinal axis of the cylindrical shape, wherein each row is defined as a pattern of alternating peaks and valleys formed by adjacent interconnected arms, wherein at least a first row, a second row, and a third row are arranged in a longitudinal direction along the longitudinal axis of the cylindrical shape, the first row being proximal to the second row and distal to the third row, wherein the first row is connected to each of the second row and the third row by a plurality of connectors extending in the longitudinal direction of the cylindrical shape to form cells that are non-quadrilateral in shape, wherein the first portion extends longitudinally from a distal end of the scaffolding structure to an intermediate location on the scaffolding structure and the second portion extends longitudinally from the intermediate location on the scaffolding structure to a proximal end of the scaffolding structure, and wherein the second portion of the scaffolding structure has a second stiffness that is less than the first stiffness; and a valve coupled to an inside diameter of the first portion of the scaffolding structure;

wherein a length of the implantable device is between about 70 mm and about 150 mm; and wherein the scaffolding structure lacks a plane of symmetry that is transverse to the longitudinal axis of the cylindrical shape.

2. The implantable device of claim 1, further comprising a plurality of eyelets configured to receive a suture, the eyelets disposed adjacent the proximal end of the scaffolding structure.

3. The implantable device of claim 2, further comprising a plurality of rounded knobs wherein the knobs are disposed adjacent the distal end of the scaffolding structure.

4. The implantable device of claim 1, further comprising a polymeric cover applied to and between the scaffolding structure.

5. The implantable device of claim 4, wherein the polymeric cover comprises a first layer and a second layer, and wherein at least one of the first and second layers comprises silicone.

6. The implantable device of claim 1, wherein the scaffolding structure comprises a memory alloy with a thickness of about 0.30 mm to about 0.60 mm.

7. The implantable device of claim 6, wherein the scaffolding structure is laser cut from a tube of nitinol.

8. The implantable device of claim 1, wherein the scaffolding structure is configured to reduce in diameter in response to an axial force applied to a longitudinal end of the implantable device in a longitudinal direction away from the implantable device.

9. The implantable device of claim 1, further comprising one or more radiopaque indicia indicating a position of the valve.

10. The implantable device of claim 1, wherein the first portion of the scaffolding structure is less compressible in a transverse direction than the second portion of the scaffolding structure.

11. The implantable device of claim 1, wherein the plurality of interconnected arms of the lattice structure of the first portion of the scaffolding structure are arranged to form quadrilateral-shaped cells.

* * * * *